US012668891B2

(12) United States Patent
Zaremba et al.

(10) Patent No.: US 12,668,891 B2
(45) Date of Patent: Jun. 30, 2026

(54) CRISPR NUCLEASE OFF-TARGET DETECTION BY SEQUENCING (CROFT-SEQ)

(71) Applicant: Vilnius University, Vilnius (LT)

(72) Inventors: Mindaugas Zaremba, Vilnius (LT);
Paulius Toliušis, Vilnius (LT);
Tautvydas Karvelis, Vilnius (LT);
Giedrius Sasnauskas, Vilnius (LT);
Tomas Šinkūnas, Vilnius (LT);
Algirdas Grybauskas, Vilnius (LT);
Arūnas Šilanskas, Vilnius (LT);
Evelina Zagorskaitė, Vilnius (LT)

(73) Assignee: Vilnius University, Vilnius (LT)

( * ) Notice: Subject to any disclaimer, the term of this patent is extended or adjusted under 35 U.S.C. 154(b) by 465 days.

(21) Appl. No.: 18/326,486

(22) Filed: May 31, 2023

(65) Prior Publication Data

US 2024/0401126 A1      Dec. 5, 2024

(51) Int. Cl.
*C40B 30/04* (2006.01)
*C12N 15/10* (2006.01)
*C12Q 1/6874* (2018.01)

(52) U.S. Cl.
CPC .......... *C40B 30/04* (2013.01); *C12N 15/1065* (2013.01); *C12Q 1/6874* (2013.01)

(58) Field of Classification Search
None
See application file for complete search history.

(56) References Cited

U.S. PATENT DOCUMENTS

2021/0147909 A1      5/2021  Deschamps et al.

OTHER PUBLICATIONS

Silva, George, et al. "Meganucleases and other tools for targeted genome engineering: perspectives and challenges for gene therapy." Current gene therapy 11.1 (2011): 11-27.
Guo, Congting, et al. "Off-target effects in CRISPR/Cas9 gene editing." Frontiers in Bioengineering and Biotechnology 11 (2023). 11 pages.
Young, Joshua, et al. "CRISPR-Cas9 editing in maize: systematic evaluation of off-target activity and its relevance in crop improvement." Scientific reports 9.1 (2019): 6729.
Hsu, Patrick D., Eric S. Lander, and Feng Zhang. "Development and applications of CRISPR-Cas9 for genome engineering." Cell 157.6 (2014): 1262-1278.
Cameron, Peter, et al. "Mapping the genomic landscape of CRISPR-Cas9 cleavage." Nature methods 14.6 (2017): 600-606.
Jinek, Martin, et al. "A programmable dual-RNA-guided DNA endonuclease in adaptive bacterial immunity." science 337.6096 (2012): 816-821.
Christian, Michelle, et al. "Targeting DNA double-strand breaks with TAL effector nucleases." Genetics 186.2 (2010): 757-761.
Kim, Yang-Gyun, Jooyeun Cha, and Srinivasan Chandrasegaran. "Hybrid restriction enzymes: zinc finger fusions to Fok I cleavage domain." Proceedings of the National Academy of Sciences 93.3 (1996): 1156-1160.
Gasiunas, Giedrius, et al. "Cas9-crRNA ribonucleoprotein complex mediates specific DNA cleavage for adaptive immunity in bacteria." Proceedings of the National Academy of Sciences 109.39 (2012): E2579-E2586.

*Primary Examiner* — Christian C Boesen

(74) *Attorney, Agent, or Firm* — Koivula & Somersalo LLC

(57)      ABSTRACT

Rapid, sensitive and cost-efficient detection and characterization method for in vitro double strand breaks produced by CRISPR-Cas9 nucleases from human genomic DNA samples.

17 Claims, 9 Drawing Sheets

Specification includes a Sequence Listing.

| Rank | Position | 1.........5..........10..........15.........20 | Reads | Δ Indels, % |
|---|---|---|---|---|
| | Target-sequence | GGAATCCCTTCTGCAGCACC | | |
| 1 | chr12:2610725-2610745 | ▓▓A▓TCCCTTCTGCAGCACC | 8484 | 0.00 |
| 2 | chr2:54626173-54626193 | GGAAT▓CTTCTGCAGC▓CC | 6902 | 0.13 |
| 3 | chr7:44036880-44036900 | G▓▓▓CCCTTCTGCAGCACC | 5302 | 0.00 |
| 4 | chr10:71703361-71703381 | ▓GAATCC▓TCT▓CAGCACC | 4852 | 0.40 |
| 5 | chr9:108705525-108705546 | ▓▓▓A▓▓CCT▓CTGCAGCACC | 3847 | 0.00 |
| 6 | chr10:42914565-42914585 | GGA▓TCCCT▓CT▓CAGCACC | 2364 | 5.66 |
| 7 | chr2:241534233-241534253 | GGAATCCC~TC▓▓CAGC▓ACC | 2091 | -0.02 |
| 8 | chr6:41489823-41489843 | ▓▓▓▓TCCCT▓CTGCAGCACC | 1986 | 0.00 |
| 9 | chr16:28603862-28603882 | GG▓▓TCCCTTCTGCAGC▓CC | 1654 | -0.39 |
| 10 | chr10:37664254-37664274 | GGA▓TCCCT▓CT▓CAGCACC | 1635 | 5.62 |
| 11 | chr10:13394771-13394791 | ▓▓ATCCCTTCTGCAGC▓CC | 1575 | 0.02 |
| 12 | chr12:115029999-115030020 | G▓▓▓TCCCTTCTGCAGC▓CC | 1540 | 0.01 |
| 13 | chr19:1180763-1180782 | G▓▓TCCCTTCTGCA~CACC | 1356 | 0.00 |
| 14 | chr13:109149774-109149794 | ▓AAT▓CCTTCTGCAG▓ACC | 1261 | -0.03 |
| 15 | chr8:101885725-101885745 | ▓▓▓TCCCT▓CTGCAGCACC | 1227 | -0.01 |
| 16 | chr19:38914955-38914975 | G▓▓TCCCTTCTGCAGC▓CC | 1058 | 0.02 |
| 17 | chr3:35071669-35071689 | ▓GAATCC▓▓▓CTGCAGCACC | 1025 | 0.00 |
| 18 | chr22:43979022-43979042 | ▓▓▓ATCCCTTCTGCAGCAC▓ | 1025 | 0.00 |
| 19 | chr16:49637110-49637130 | GGA▓TCCCT▓CTGCAGCACC | 992 | 0.98 |
| 20 | chr11:47532479-47532501 | GGAATCCCTTCT▓CAGCA▓▓ | 981 | -0.02 |
| 21 | chr10:3109798-3109819 | ▓▓▓T▓CCTTCTGCAGCACC | 827 | -0.01 |
| 22 | chr3:10844197-10844218 | ▓▓▓TCCCTTCTGCA▓GCACC | 777 | 0.00 |
| 23 | chr13:114050110-114050131 | GG▓▓CCCTTC▓GCAGCA▓C | 761 | 0.79 |
| 24 | chr18:8707526-8707546 | GGAA▓CC▓TCTGCAGCACC | 735 | 43.43 |
| 25 | chr11:66707556-66707576 | GGAA▓CCTTCTGCAGC▓CC | 727 | -0.11 |
| 26 | chr7:102016276-102016296 | ▓▓A▓CCCTTCTGCAGCACC | 718 | -0.01 |
| 27 | chr9:110400010-110400030 | ▓AATCCCTTC▓GCAGCACC | 706 | 0.41 |
| 28 | chr3:123322634-123322654 | ▓▓A▓TCCCT▓CTGCAGCACC | 628 | 0.01 |
| 29 | chr9:121863911-121863942 | ▓GAATCCCT▓CTGCAGC▓C▓▓ | 572 | -0.01 |
| 30 | chr10:7754681-7754702 | ▓▓▓T▓CCTTC▓GCAGCACC | 568 | -0.02 |
| 31 | chr22:18817094-18817115 | ▓GA▓▓CCCTTCTG▓AGCACC | 548 | 0.00 |
| 32 | chr6:142048404-142048424 | G▓▓TCCCT▓C▓GCAGCACC | 498 | -0.09 |
| 33 | chr20:46274930-46274951 | ▓▓ATCCCT▓CTG▓CAGCACC | 479 | -0.01 |
| 34 | chr13:99359192-99359213 | G▓▓CT▓CCTTC▓GCAGCACC | 458 | 0.01 |
| 35 | chr5:69042692-69042712 | ▓▓ATCC▓TTCTGCAGCACC | 450 | 0.00 |
| 36 | chr17:80950160-80950180 | ▓GA▓CCC▓TCTGCAGCACC | 446 | 0.63 |
| 37 | chr4:140590969-140590989 | ▓GAATC▓CTTCT▓CA▓CACC | 426 | 0.02 |
| 38 | chr11:22625788-22625808 | GGAATCCCTTCTGCAGCACC | 413 | 85.40 |

Fig. 3

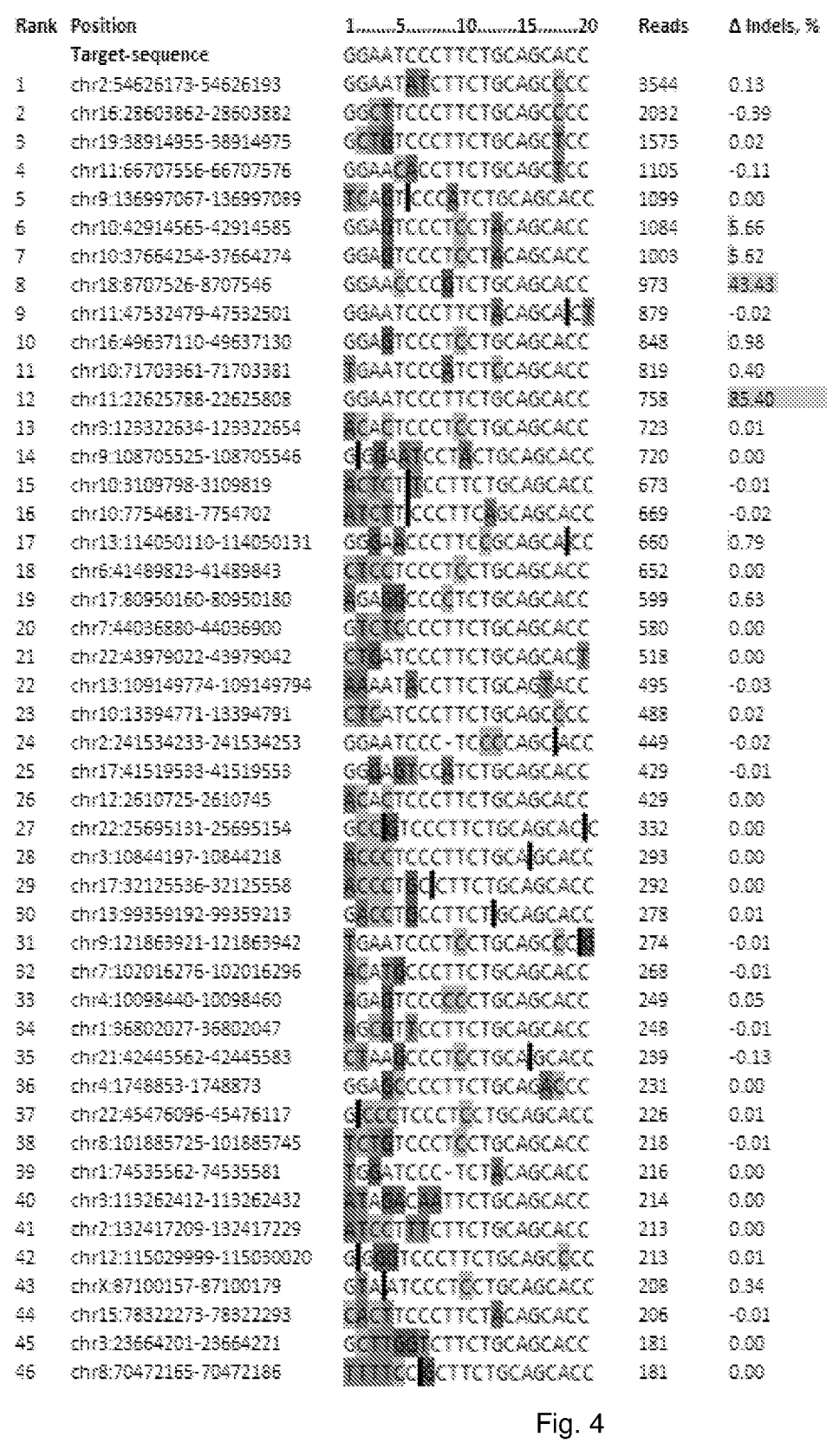

| Rank | Position | 1.......5..........10.......15.........20 | Reads | Δ Indels, % |
|---|---|---|---|---|
| | Target-sequence | GGAATCCCTTCTGCAGCACC | | |
| 1 | chr2:54626173-54626193 | GGAAT CTTCTGCAGC CC | 3544 | 0.13 |
| 2 | chr16:28603862-28603882 | GG TCCCTTCTGCAGC CC | 2032 | -0.39 |
| 3 | chr19:38914955-38914975 | G TCCCTTCTGCAGC CC | 1575 | 0.02 |
| 4 | chr11:66707556-66707576 | GGAA CCTTCTGCAGC CC | 1105 | -0.11 |
| 5 | chr9:136997067-136997089 | A T CC TCTGCAGCACC | 1099 | 0.00 |
| 6 | chr10:42914565-42914585 | GGA TCCCT CT CAGCACC | 1084 | 5.66 |
| 7 | chr10:37664254-37664274 | GGA TCCCT CT CAGCACC | 1003 | 5.62 |
| 8 | chr18:8707526-8707546 | GGAA CCC TCTGCAGCACC | 973 | 85.43 |
| 9 | chr11:47532479-47532501 | GGAATCCCTTCT CAGCA C | 879 | -0.02 |
| 10 | chr16:49637110-49637130 | GGA TCCCT CTGCAGCACC | 848 | 0.98 |
| 11 | chr10:71703361-71703381 | GAATCC TCT CAGCACC | 819 | 0.48 |
| 12 | chr11:22625788-22625808 | GGAATCCCTTCTGCAGCACC | 758 | 85.40 |
| 13 | chr3:123322634-123322654 | A TCCCT CTGCAGCACC | 723 | 0.01 |
| 14 | chr9:108705525-108705546 | C A CCT CTGCAGCACC | 720 | 0.00 |
| 15 | chr10:3189798-3109819 | CCT CCTTCTGCAGCACC | 673 | -0.01 |
| 16 | chr10:7754681-7754702 | T CCCTTC CAGCACC | 669 | -0.02 |
| 17 | chr13:114050110-114050131 | GG A CCCTTC GCAGCA CC | 660 | 0.79 |
| 18 | chr6:41489823-41489843 | CCTCCCT CTGCAGCACC | 652 | 0.00 |
| 19 | chr17:80950160-80950180 | GA CCC TCTGCAGCACC | 599 | 0.63 |
| 20 | chr7:44036880-44036900 | G CCCTTCTGCAGCACC | 580 | 0.00 |
| 21 | chr22:43979022-43979042 | ATCCCTTCTGCAGCAC | 518 | 0.00 |
| 22 | chr13:109149774-109149794 | AAT CCTTCTGCAG ACC | 495 | -0.03 |
| 23 | chr10:13394771-13394791 | ATCCCTTCTGCAGC CC | 488 | 0.02 |
| 24 | chr2:241534233-241534253 | GGAATCCC-TC CAGC ACC | 449 | -0.02 |
| 25 | chr17:41519533-41519553 | GG A CC TCTGCAGCACC | 429 | -0.01 |
| 26 | chr12:2610725-2610745 | CA TCCCTTCTGCAGCACC | 429 | 0.00 |
| 27 | chr22:25695131-25695154 | G TCCCTTCTGCAGCAC | 332 | 0.00 |
| 28 | chr3:10844197-10844218 | CCTCCCTTCTGCA GCACC | 293 | 0.00 |
| 29 | chr17:32125536-32125558 | CCCT CTTCTGCAGCACC | 292 | 0.00 |
| 30 | chr13:99359192-99359213 | CCTCCCTTCT CAGCACC | 278 | 0.01 |
| 31 | chr9:121863921-121863942 | GAATCCCT CTGCAGC C | 274 | -0.01 |
| 32 | chr7:102016276-102016296 | CA CCCTTCTGCAGCACC | 268 | -0.01 |
| 33 | chr4:10098440-10098460 | GA TCCC CTGCAGCACC | 249 | 0.05 |
| 34 | chr1:36802027-36802047 | G T CCTTCTGCAGCACC | 248 | -0.01 |
| 35 | chr21:42445562-42445583 | AA CCCT CTGCA GCACC | 239 | -0.13 |
| 36 | chr4:1748853-1748873 | GGA CCCTTCTGCAG CC | 231 | 0.00 |
| 37 | chr22:45476096-45476117 | C TCCCT CTGCAGCACC | 226 | 0.01 |
| 38 | chr8:101885725-101885745 | G TCCCT CTGCAGCACC | 218 | -0.01 |
| 39 | chr1:74535562-74535581 | GAATCCC-TCT CAGCACC | 216 | 0.00 |
| 40 | chr3:113262412-113262432 | A C TTCTGCAGCACC | 214 | 0.00 |
| 41 | chr2:132417209-132417229 | CCT CTTCTGCAGCACC | 213 | 0.00 |
| 42 | chr12:115029999-115030020 | C TCCCTTCTGCAGC CC | 213 | 0.01 |
| 43 | chrX:87100157-87100179 | G A TCCCT CTGCAGCACC | 208 | 0.34 |
| 44 | chr15:78322273-78322293 | C TCCCTTCT CAGCACC | 206 | -0.01 |
| 45 | chr3:23664201-23664221 | G C CTTCTGCAGCACC | 181 | 0.00 |
| 46 | chr8:70472165-70472186 | C CTTCTGCAGCACC | 181 | 0.00 |

Fig. 4

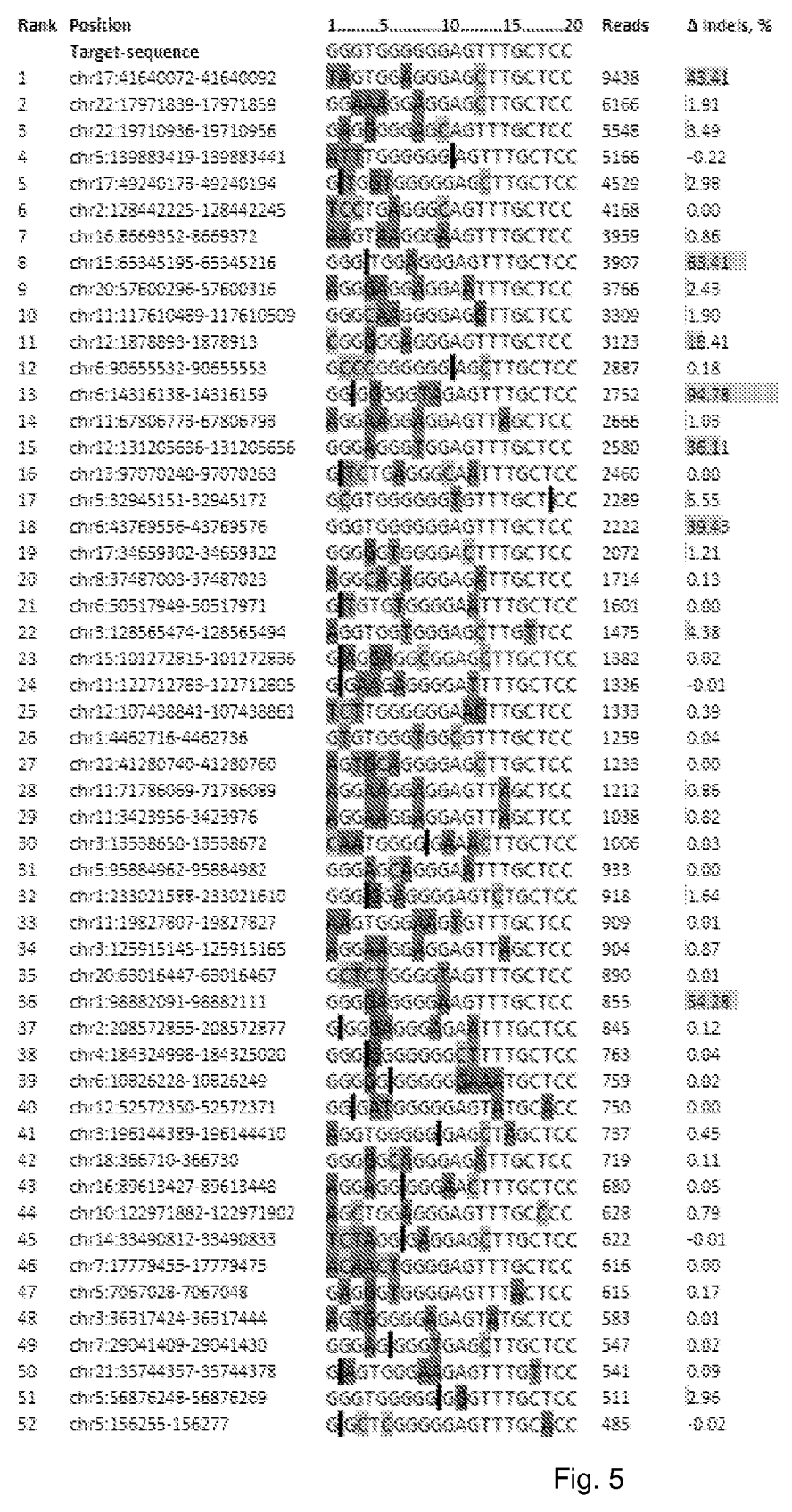

| Rank | Position | 1........5.........10.........15.........20 | Reads | Δ Indels, % |
|---|---|---|---|---|
| | Target-sequence | GGGTGGGGGGAGTTTGCTCC | | |
| 1 | chr17:41640072-41640092 | | 9438 | |
| 2 | chr22:17971839-17971859 | | 6166 | 1.91 |
| 3 | chr22:19710936-19710956 | | 5548 | 3.49 |
| 4 | chr5:139883419-139883441 | | 5166 | -0.22 |
| 5 | chr17:49240173-49240194 | | 4529 | 2.98 |
| 6 | chr2:128442225-128442245 | | 4168 | 0.00 |
| 7 | chr16:8669352-8669372 | | 3959 | 0.86 |
| 8 | chr15:65345195-65345216 | | 3907 | |
| 9 | chr20:57600296-57600316 | | 3766 | 2.43 |
| 10 | chr11:117610489-117610509 | | 3309 | 1.90 |
| 11 | chr12:1878893-1878913 | | 3123 | 18.41 |
| 12 | chr6:90655532-90655553 | | 2887 | 0.18 |
| 13 | chr6:14316138-14316159 | | 2752 | |
| 14 | chr11:67806773-67806793 | | 2666 | 1.05 |
| 15 | chr12:131205636-131205656 | | 2580 | 36.11 |
| 16 | chr13:97070240-97070263 | | 2460 | 0.02 |
| 17 | chr5:32945151-32945172 | | 2289 | 5.55 |
| 18 | chr6:43769556-43769576 | | 2222 | |
| 19 | chr17:34659302-34659322 | | 2072 | 1.21 |
| 20 | chr8:37487003-37487023 | | 1714 | 0.13 |
| 21 | chr6:50517949-50517971 | | 1601 | 0.00 |
| 22 | chr3:128565474-128565494 | | 1475 | 4.38 |
| 23 | chr15:101272815-101272836 | | 1382 | 0.02 |
| 24 | chr11:122712783-122712805 | | 1336 | -0.01 |
| 25 | chr12:107438841-107438861 | | 1333 | 0.39 |
| 26 | chr1:4462716-4462736 | | 1259 | 0.04 |
| 27 | chr22:41280740-41280760 | | 1233 | 0.00 |
| 28 | chr11:71786069-71786089 | | 1212 | 0.86 |
| 29 | chr11:3423956-3423976 | | 1038 | 0.82 |
| 30 | chr3:13558650-13558672 | | 1006 | 0.03 |
| 31 | chr5:95884962-95884982 | | 933 | 0.00 |
| 32 | chr1:233021588-233021610 | | 918 | 1.64 |
| 33 | chr11:19827807-19827827 | | 909 | 0.01 |
| 34 | chr3:125915145-125915165 | | 904 | 0.87 |
| 35 | chr20:63016447-63016467 | | 890 | 0.01 |
| 36 | chr1:98882091-98882111 | | 855 | |
| 37 | chr2:208572855-208572877 | | 845 | 0.12 |
| 38 | chr4:184324998-184325020 | | 763 | 0.04 |
| 39 | chr6:18826228-18826249 | | 759 | 0.02 |
| 40 | chr12:52572350-52572371 | | 750 | 0.00 |
| 41 | chr3:196144389-196144410 | | 737 | 0.45 |
| 42 | chr18:366710-366730 | | 719 | 0.11 |
| 43 | chr16:89613427-89613448 | | 680 | 0.05 |
| 44 | chr10:122971882-122971902 | | 628 | 0.79 |
| 45 | chr14:33490812-33490833 | | 622 | -0.01 |
| 46 | chr7:17779455-17779475 | | 616 | 0.00 |
| 47 | chr5:7067028-7067048 | | 615 | 0.17 |
| 48 | chr3:36317424-36317444 | | 583 | 0.01 |
| 49 | chr7:29041409-29041430 | | 547 | 0.02 |
| 50 | chr21:35744357-35744378 | | 541 | 0.09 |
| 51 | chr5:56876248-56876269 | | 511 | 2.96 |
| 52 | chr5:156255-156277 | | 485 | -0.02 |

Fig. 5

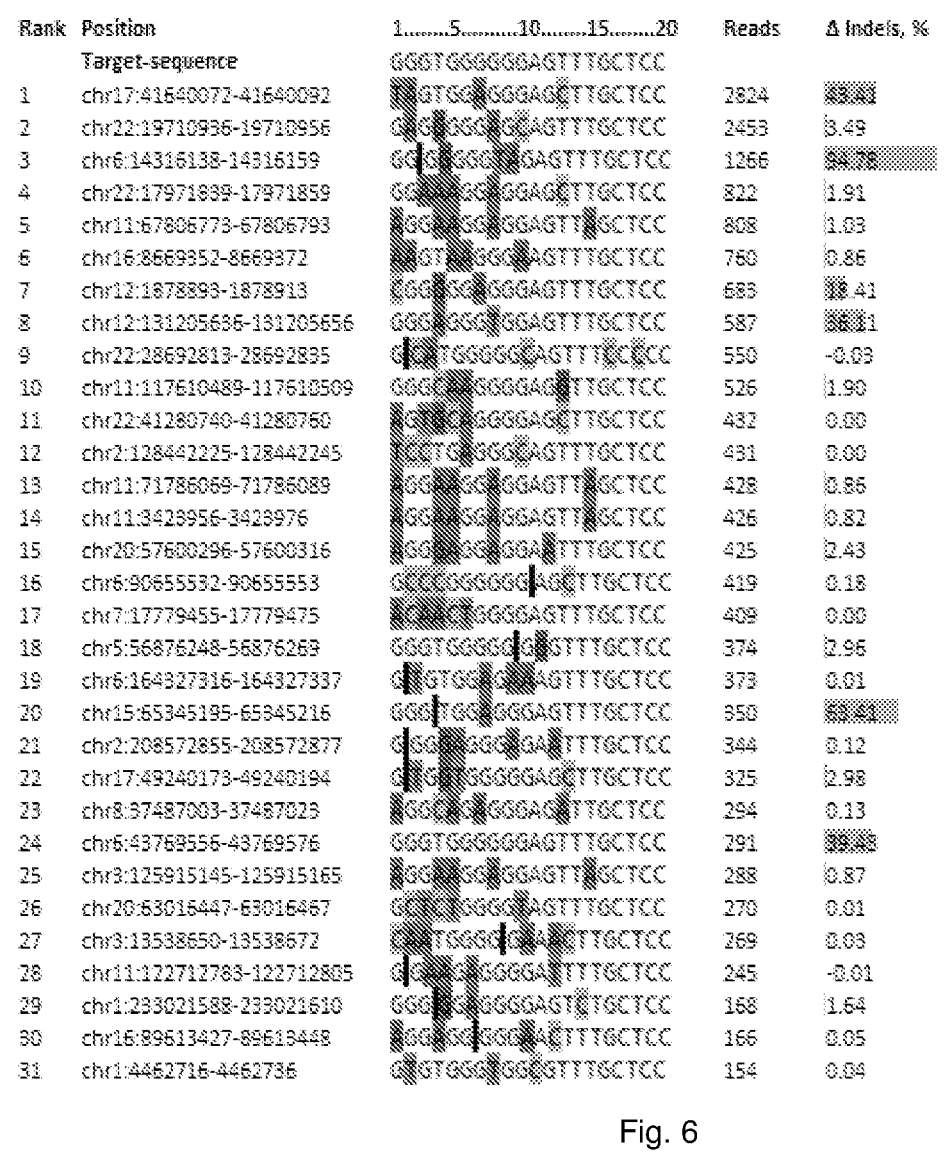

| Rank | Position | 1........5..........10.........15..........20 | Reads | Δ Indels, % |
|---|---|---|---|---|
| | Target-sequence | GGGTGGGGGGAGTTTGCTCC | | |
| 1 | chr17:41640072-41640092 | ▓GTG▓GGGAG▓TTGCTCC | 2824 | ▓▓▓ |
| 2 | chr22:19710936-19710956 | G▓C▓GGG▓G▓AGTTTGCTCC | 2453 | 3.49 |
| 3 | chr6:14316138-14316159 | GG▓▓GGG▓GAGTTTGCTCC | 1266 | ▓▓▓ |
| 4 | chr22:17971839-17971859 | GG▓▓GG▓GGGAG▓TTGCTCC | 822 | 1.91 |
| 5 | chr11:67806773-67806793 | ▓GG▓GGG▓GGAGTT▓GCTCC | 808 | 1.83 |
| 6 | chr16:8669352-8669372 | ▓▓GT▓GGG▓AGTTTGCTCC | 760 | 0.86 |
| 7 | chr12:1878893-1878913 | ▓GG▓GG▓GGGAGTTTGCTCC | 683 | ▓▓.41 |
| 8 | chr12:131205636-131205656 | GGG▓GGG▓GGAGTTTGCTCC | 587 | ▓▓▓1 |
| 9 | chr22:28692813-28692835 | G▓▓TGGGGG▓AGTTT▓C▓CC | 550 | -0.03 |
| 10 | chr11:117610489-117610509 | GGG▓▓GGGGAG▓TTGCTCC | 526 | 1.90 |
| 11 | chr22:41280740-41280760 | ▓G▓▓G▓GGGGAG▓TTGCTCC | 432 | 0.80 |
| 12 | chr2:128442225-128442245 | ▓CCTG▓GGG▓AGTTTGCTCC | 431 | 0.00 |
| 13 | chr11:71786069-71786089 | ▓GG▓▓GG▓GGAGTT▓GCTCC | 428 | 0.86 |
| 14 | chr11:3423956-3423976 | ▓GG▓▓GG▓GGAGTT▓GCTCC | 426 | 0.82 |
| 15 | chr20:57600296-57600316 | ▓GG▓▓GG▓GGA▓TTTGCTCC | 425 | 2.43 |
| 16 | chr6:90655532-90655553 | G▓▓C▓GGGGG▓AG▓TTGCTCC | 419 | 0.18 |
| 17 | chr7:17779455-17779475 | ▓▓▓▓C▓GGGGAGTTTGCTCC | 409 | 0.80 |
| 18 | chr5:56876248-56876269 | GGGTGGGG▓G▓GTTTGCTCC | 374 | 2.96 |
| 19 | chr6:164327316-164327337 | G▓GTGG▓G▓AGTTTGCTCC | 373 | 0.01 |
| 20 | chr15:65345195-65345216 | GGG▓GG▓GGGAGTTTGCTCC | 350 | ▓▓▓ |
| 21 | chr2:208572855-208572877 | G▓G▓▓AG▓GA▓TTTGCTCC | 344 | 0.12 |
| 22 | chr17:49240173-49240194 | G▓▓C▓GGGGAG▓TTGCTCC | 325 | 2.98 |
| 23 | chr8:37487003-37487023 | ▓GG▓▓GGGGAG▓TTGCTCC | 294 | 0.13 |
| 24 | chr6:43769556-43769576 | GGGTGGGGGGAGTTTGCTCC | 291 | ▓▓▓ |
| 25 | chr3:125915145-125915165 | ▓GG▓GG▓GGAGTT▓GCTCC | 288 | 0.87 |
| 26 | chr20:63016447-63016467 | G▓▓▓GGGG▓AGTTTGCTCC | 270 | 0.01 |
| 27 | chr3:13538650-13538672 | G▓GTGGG▓G▓A▓TTGCTCC | 269 | 0.03 |
| 28 | chr11:122712783-122712805 | G▓▓▓▓GGGGA▓TTTGCTCC | 245 | -0.01 |
| 29 | chr1:233021588-233021610 | GGG▓▓GGGGAGT▓TGCTCC | 168 | 1.64 |
| 30 | chr16:89613427-89613448 | ▓GG▓GG▓GGG▓▓TTTGCTCC | 166 | 0.05 |
| 31 | chr1:4462716-4462736 | G▓GTGG▓GG▓GTTTGCTCC | 154 | 0.04 |

Fig. 6

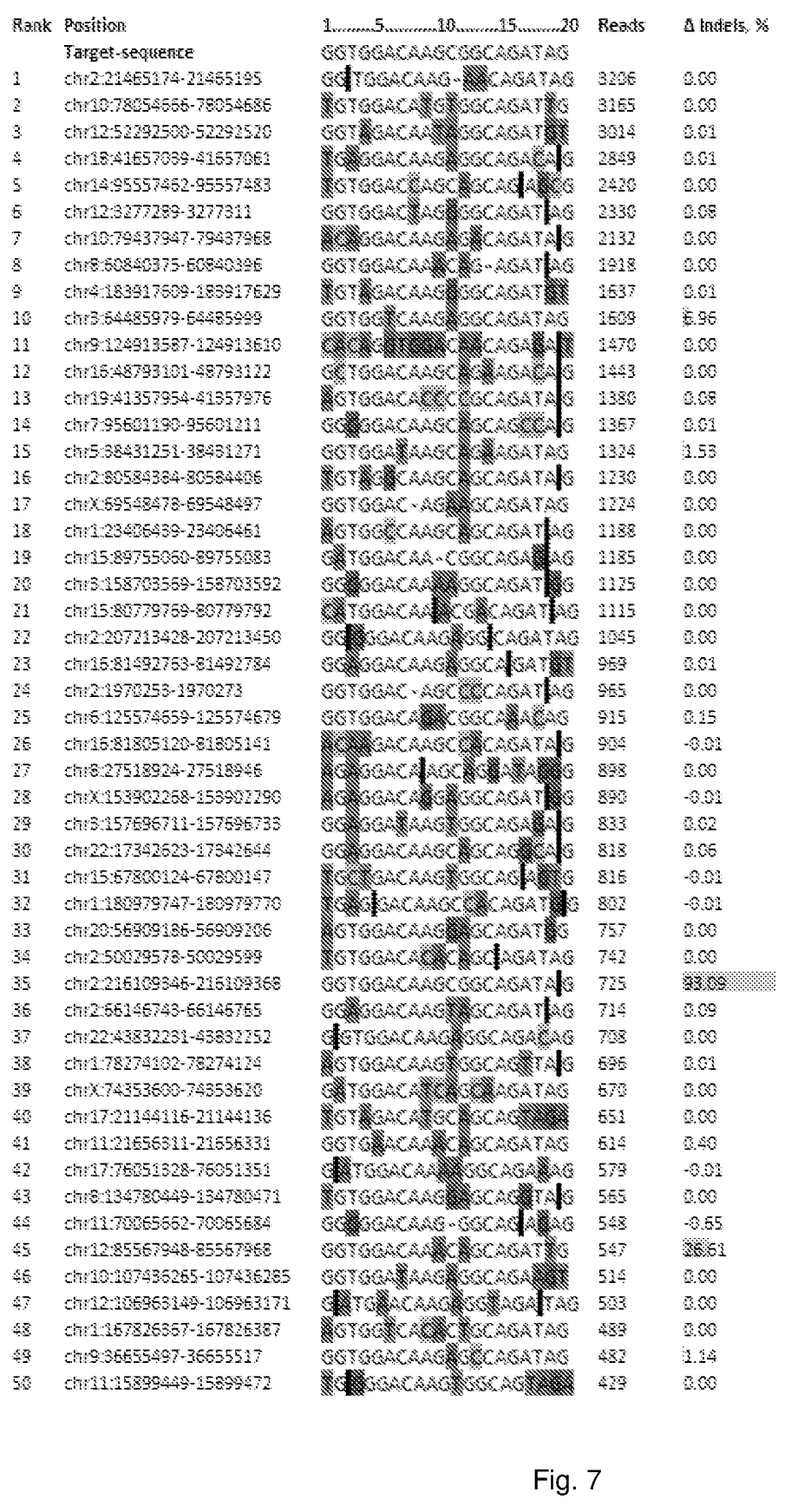

| Rank | Position | 1.......5.......10.......15.......20 | Reads | Δ Indels, % |
|---|---|---|---|---|
| | Target-sequence | GGTGGACAAGCGGCAGATAG | | |
| 1 | chr2:21465174-21465195 | GG TGGACAAG- CAGATAG | 3206 | 0.00 |
| 2 | chr10:78054666-78054686 | GTGGACA G GGCAGAT G | 3165 | 0.00 |
| 3 | chr12:52292500-52292520 | GGT GACAA GGCAGAT | 3014 | 0.01 |
| 4 | chr18:41657039-41657061 | G GGACAAG GGCAGA A G | 2849 | 0.01 |
| 5 | chr14:95557462-95557483 | GTGGAC AGC GCA A G | 2420 | 0.00 |
| 6 | chr12:3277289-3277311 | GGTGGAC AG GGCAGAT AG | 2330 | 0.08 |
| 7 | chr10:79437947-79437968 | GGACAAG CAGATA G | 2132 | 0.00 |
| 8 | chr8:60840375-60840396 | GGTGGACAA G- AGATAG | 1918 | 0.00 |
| 9 | chr4:183917609-183917629 | GT ACAAG GGCAGAT | 1637 | 0.01 |
| 10 | chr3:64485979-64485999 | GGTGG CAAG GGCAGATAG | 1609 | 6.96 |
| 11 | chr9:124913587-124913610 | C CAGA G | 1470 | 0.00 |
| 12 | chr16:48793101-48793122 | G TGGACAAGC AGAC G | 1443 | 0.00 |
| 13 | chr19:41357954-41357976 | GTGGACA C GGCAGATA G | 1380 | 0.08 |
| 14 | chr7:95601190-95601211 | GG GGACAAGC GCAG CA G | 1367 | 0.01 |
| 15 | chr5:38431251-38431271 | GGTGGA AAGC AGATAG | 1324 | 1.53 |
| 16 | chr2:80584384-80584406 | GT C CAAGC GCAGATA G | 1230 | 0.00 |
| 17 | chrX:69548478-69548497 | GGTGGAC- AG GCAGATAG | 1224 | 0.00 |
| 18 | chr1:23406439-23406461 | GTGG CAAGC GCAGAT AG | 1188 | 0.00 |
| 19 | chr15:89755060-89755083 | G TGGACAA- CGGCAGA AG | 1185 | 0.00 |
| 20 | chr3:158703569-158703592 | GG GGACAA GGCAGAT G | 1125 | 0.00 |
| 21 | chr15:80779769-80779792 | TGGACAA CG CAGAT AG | 1115 | 0.00 |
| 22 | chr2:207213428-207213450 | GG GGACAAG GG CAGATAG | 1045 | 0.00 |
| 23 | chr16:81492763-81492784 | GG GGACAAG GGCA GAT | 969 | 0.01 |
| 24 | chr2:1970253-1970273 | GGTGGAC- AGC CAGAT AG | 965 | 0.00 |
| 25 | chr6:125574659-125574679 | GGTGGACA CGGCA A AG | 915 | 0.15 |
| 26 | chr16:81805120-81805141 | GGACAAGC CAGATA G | 934 | -0.01 |
| 27 | chr8:27518924-27518946 | G GGACA AGC G A A G | 898 | 0.00 |
| 28 | chrX:153902268-153902290 | GGACA GGCAGAT G | 893 | -0.01 |
| 29 | chr3:157696711-157696733 | GG GGA AAG GGCAGA AG | 833 | 0.02 |
| 30 | chr22:17342623-17342644 | GG GGACAAGC GCAG A G | 818 | 0.06 |
| 31 | chr15:67800124-67800147 | GC GACAAG GGCAG G | 816 | -0.01 |
| 32 | chr1:180979747-180979770 | C A GACAAGC CAGAT G | 802 | -0.01 |
| 33 | chr20:56909186-56909206 | GTGGACAAG GCAGAT G | 757 | 0.00 |
| 34 | chr2:50029578-50029599 | GTGGACA C G GCAGATAG | 742 | 0.00 |
| 35 | chr2:216109346-216109368 | GGTGGACAAGCGGCAGATA G | 725 | 33.09 |
| 36 | chr2:66146743-66146765 | GG GGACAAG GCAGAT AG | 714 | 0.09 |
| 37 | chr22:43832231-43832252 | G TGGACAAG GGCAGA AG | 708 | 0.00 |
| 38 | chr1:78274102-78274124 | GTGGACAAG GGCAG TA G | 696 | 0.01 |
| 39 | chrX:74353600-74353620 | G TGGACA G GCAGATAG | 670 | 0.00 |
| 40 | chr17:21144116-21144136 | GT GACA GC GCAG | 651 | 0.00 |
| 41 | chr11:21656311-21656331 | GGTG ACAA GCAGATAG | 614 | 0.40 |
| 42 | chr17:76051328-76051351 | G TGGACAA GGCAGA AG | 579 | -0.01 |
| 43 | chr8:134780449-134780471 | GTGGACAAG GCAG TA G | 565 | 0.00 |
| 44 | chr11:70065662-70065684 | GG GGACAAG- GGCAG A AG | 548 | -0.65 |
| 45 | chr12:85567948-85567968 | GGTGGACAA C GCAGAT G | 547 | 35.61 |
| 46 | chr10:107436265-107436285 | GGTGGA AAG GGCAGA | 514 | 0.00 |
| 47 | chr12:106963149-106963171 | G TG ACAAG GG AGA TAG | 503 | 0.00 |
| 48 | chr1:167826367-167826387 | GTGG AC C GCAGATAG | 489 | 0.00 |
| 49 | chr9:36655497-36655517 | GGTGGACAAG GGCAGATAG | 482 | 1.14 |
| 50 | chr11:15899449-15899472 | GGACAAG GGCAG | 429 | 0.00 |

Fig. 7

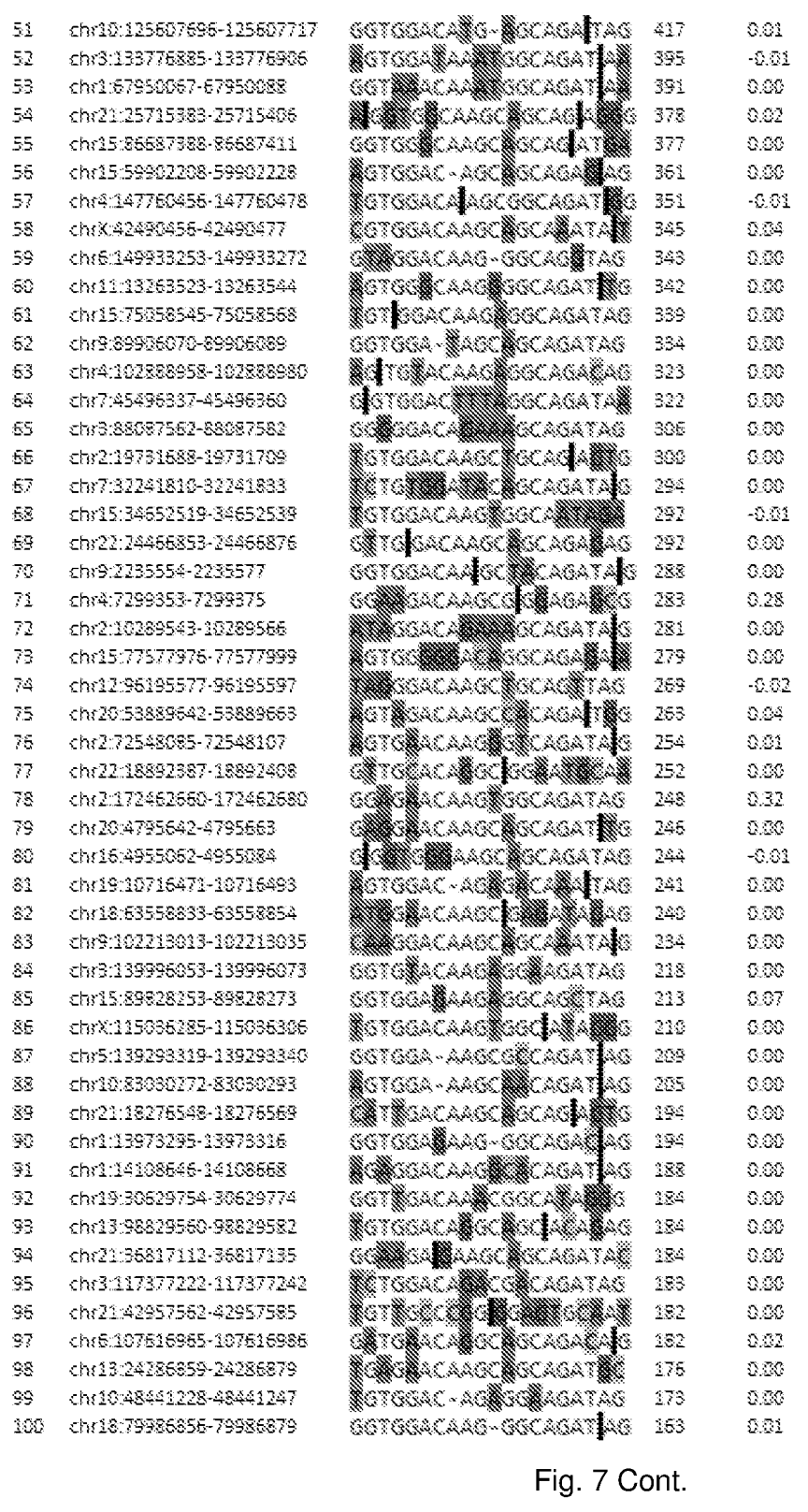

| | | | | |
|---|---|---|---|---|
| 51 | chr10:125607696-125607717 | GGTGGACAAG~AGCAGATTAG | 417 | 0.01 |
| 52 | chr3:133776885-133776906 | AGTGGAAAAAGGCAGATAA | 395 | -0.01 |
| 53 | chr1:67950067-67950088 | GGTAACAAAGGCAGATAA | 391 | 0.00 |
| 54 | chr21:25715383-25715406 | AAACGCAAGCACAGAAG | 378 | 0.02 |
| 55 | chr15:86687388-86687411 | GGTGCCAAGCAGGCAGAT | 377 | 0.00 |
| 56 | chr15:59902208-59902228 | AGTGGAC~AGCAGCAGAAAG | 361 | 0.00 |
| 57 | chr4:147760456-147760478 | AGTGGACAAAGCGGCAGATAG | 351 | -0.01 |
| 58 | chrX:42490456-42490477 | AGTGGACAAGCAGCAATATA | 345 | 0.04 |
| 59 | chr6:149933253-149933272 | GAGGACAAG~GGCAGATAG | 343 | 0.00 |
| 60 | chr11:13263523-13263544 | AGTGCACAAGAGGCAGATAG | 342 | 0.00 |
| 61 | chr15:75058545-75058568 | AGTAGACAAGAGGCAGATAG | 339 | 0.00 |
| 62 | chr9:89906070-89906089 | GGTGGA~AAGCAGCAGATAG | 334 | 0.00 |
| 63 | chr4:102388958-102388980 | ACTGACAAGAGGCAGAAAG | 323 | 0.00 |
| 64 | chr7:45496337-45496360 | CAGTGGACAAGGCAGATAA | 322 | 0.00 |
| 65 | chr3:88087562-88087582 | GCAGGACAAAGCAGATAG | 306 | 0.00 |
| 66 | chr2:19731688-19731709 | AGTGGACAAGCAGCAAAAG | 300 | 0.00 |
| 67 | chr7:32241810-32241833 | AATGAAAAAGCGGCAGATAG | 294 | 0.00 |
| 68 | chr15:34652519-34652539 | AGTGGACAAGAGGCAAAA | 292 | -0.01 |
| 69 | chr22:24466853-24466876 | CATGAGACAAGCAGCAGAAAG | 292 | 0.00 |
| 70 | chr9:2235554-2235577 | GGTGGACAAAGCAACAGATAAG | 288 | 0.00 |
| 71 | chr4:7299353-7299375 | GCAAGACAAGCGAAAGAAAAG | 283 | 0.28 |
| 72 | chr2:10289543-10289566 | AAAAGACAAAGCAGCAGATAG | 281 | 0.00 |
| 73 | chr15:77577976-77577999 | GTGCAAAGAGGCAGAAAAA | 279 | 0.00 |
| 74 | chr12:96195577-96195597 | AAAGGACAAGCAGCAGATAG | 269 | -0.02 |
| 75 | chr20:53889642-53889663 | GTAGACAAGCAAGCAGATAAG | 263 | 0.04 |
| 76 | chr2:72548085-72548107 | AGTGAACAAGAGGCAGATAG | 254 | 0.01 |
| 77 | chr22:18892387-18892408 | CATGGACAAGCAGCAAAGAA | 252 | 0.00 |
| 78 | chr2:172462660-172462680 | GCAGGACAAGAGGCAGATAG | 248 | 0.32 |
| 79 | chr20:4795642-4795663 | CAAGGACAAGCAGCAGATAG | 246 | 0.00 |
| 80 | chr16:4955062-4955084 | CAAACAAGCAGGCAGATAG | 244 | -0.01 |
| 81 | chr19:10716471-10716493 | AGTGGAC~AGCAGCAAATAG | 241 | 0.00 |
| 82 | chr18:63558833-63558854 | AAAACAAGCAAAAATAAG | 240 | 0.00 |
| 83 | chr9:102213013-102213035 | AGGACAAGCAGGCAAATAG | 234 | 0.00 |
| 84 | chr3:139996053-139996073 | GGTGAACAAGAGGAGATAG | 218 | 0.00 |
| 85 | chr15:89828253-89828273 | GGTGGAAAAGAGGCAGATAG | 213 | 0.07 |
| 86 | chrX:115036285-115036306 | AGTGGACAAGAGGCAAAAAG | 210 | 0.00 |
| 87 | chr5:139293319-139293340 | GGTGGA~AAGCGACAGATAG | 209 | 0.00 |
| 88 | chr10:83030272-83030293 | AGTGGA~AAGCAGCAGATAG | 205 | 0.00 |
| 89 | chr21:18276548-18276569 | CATGACAAGCAGCAGAAAG | 194 | 0.00 |
| 90 | chr1:13973295-13973316 | GGTGGAAAAG~GGCAGAGAG | 194 | 0.00 |
| 91 | chr1:14108646-14108668 | AAGGACAAGAGCAGATAG | 188 | 0.00 |
| 92 | chr19:30629754-30629774 | GGTAGACAAACGGCAAAAG | 184 | 0.00 |
| 93 | chr13:98829560-98829582 | AGTGGACAAGCAGCAAAAAG | 184 | 0.00 |
| 94 | chr21:36817112-36817135 | GCAAGAAAAGCAGCAGATAA | 184 | 0.00 |
| 95 | chr3:117377222-117377242 | AGTGGACAACGACAGATAG | 183 | 0.00 |
| 96 | chr21:42957562-42957585 | AGTAGCACAAACAAGGAA | 182 | 0.00 |
| 97 | chr6:107616965-107616986 | CATGACAAGCAGCAGACAG | 182 | 0.02 |
| 98 | chr13:24286859-24286879 | ACAGACAAGCAGCAGAT | 176 | 0.00 |
| 99 | chr10:48441228-48441247 | AGTGGAC~AGAGGAGATAG | 173 | 0.00 |
| 100 | chr18:79986856-79986879 | GGTGGACAAG~GGCAGATAG | 163 | 0.01 |

Fig. 7 Cont.

| Rank | Position | 1........5..........10........15.........20 | Reads | Δ Indels, % |
|------|----------|--------------------------------------------|-------|-------------|
| | Target-sequence | GGTGGACAAGCGGCAGATAG | | |
| 1 | chr18:78054666-78054686 | GGTGGACAAGCGGCAGATAG | 4248 | 0.00 |
| 2 | chr22:43832231-43832252 | GGTGGACAAGCGGCAGACAG | 3875 | 0.00 |
| 3 | chr18:41657039-41657061 | GGTGGACAAGCGGCAGACAG | 2009 | 0.01 |
| 4 | chr18:79437947-79437968 | GGGGGACAAGCGGCAGATAG | 1912 | 0.00 |
| 5 | chr14:95557462-95557483 | GGTGGACAAGCGGCAGAGAG | 1830 | 0.00 |
| 6 | chr2:172462660-172462680 | GGGGACAAGCGGCAGATAG | 794 | 0.32 |
| 7 | chr4:7299353-7299375 | GGGGACAAGCGGAGAGAG | 780 | 0.28 |
| 8 | chr9:124913587-124913610 | GGGGCAGCCAGAGAG | 764 | 0.00 |
| 9 | chr3:158703569-158703592 | GGGGACAAGCGGCAGATAG | 733 | 0.00 |
| 10 | chr8:60840375-60840396 | GGTGGACAAGCGG-AGATAG | 708 | 0.00 |
| 11 | chr2:1970253-1970273 | GGTGGAC-AGCGGCAGATAG | 699 | 0.00 |
| 12 | chr16:48793101-48793122 | GGTGGACAAGCGGAGACAG | 683 | 0.00 |
| 13 | chr12:3277289-3277311 | GGTGGACAAGCGGCAGATAG | 662 | 0.08 |
| 14 | chr15:80779769-80779792 | GGTGGACAAGCGGCAGATAG | 599 | 0.00 |
| 15 | chr2:21465174-21465195 | GGTGGACAAG-GCAGATAG | 570 | 0.00 |
| 16 | chr1:167826367-167826387 | GGTGGCAGCCGGCAGATAG | 526 | 0.00 |
| 17 | chr11:21656311-21656331 | GGTGGACAAGCGGCAGATAG | 520 | 0.40 |
| 18 | chr1:22122796-22122819 | GGTGGCAGCGGCAG | 470 | 0.00 |
| 19 | chr3:64485979-64485999 | GGTGGCAAGCGGCAGATAG | 451 | 8.96 |
| 20 | chr6:125574659-125574679 | GGTGGACAGCGGCAGATAG | 434 | 0.15 |
| 21 | chr1:110486109-110486132 | GGTGGACAAGCGGCAG | 422 | -0.01 |
| 22 | chr4:89007090-89007113 | GGGGGACAAGCGGCAGAGAG | 408 | 0.00 |
| 23 | chr3:133776885-133776906 | GGTGGACAAGCGGCAGATAG | 402 | -0.01 |
| 24 | chr15:67800124-67800147 | GGGGACAAGCGGCAGATAG | 388 | -0.01 |
| 25 | chr19:41357954-41357976 | GGTGGACAGCCGGCAGATAG | 379 | 0.08 |
| 26 | chr15:89828253-89828273 | GGTGGACAAGCGGCAGATAG | 342 | 0.07 |
| 27 | chr5:38431251-38431271 | GGTGGACAAGCGGCAGATAG | 309 | 1.53 |
| 28 | chr1:180979747-180979770 | GGGGACAAGCGGCAGATAG | 308 | -0.01 |
| 29 | chr2:66146743-66146765 | GGGGGACAAGCGGCAGATAG | 297 | 0.09 |
| 30 | chr13:24286859-24286879 | GGGGACAAGCGGCAGAT | 286 | 0.00 |
| 31 | chr12:85567948-85567968 | GGTGGACAAGCGGCAGATAG | 278 | 26.61 |
| 32 | chr9:36655497-36655517 | GGTGGACAAGCGGCAGATAG | 276 | 1.14 |
| 33 | chr12:52292500-52292520 | GGTGGACAAGGGCAGAT | 251 | 0.01 |
| 34 | chr20:4795642-4795663 | GGGGACAAGCGGCAGATAG | 246 | 0.00 |
| 35 | chr2:207213428-207213450 | GGGGGACAAGCGGCAGATAG | 243 | 0.00 |
| 36 | chr21:25715383-25715406 | GGGGCAAGCGGCAGATAG | 235 | 0.02 |

Fig. 8

SEQUENCE LISTING

```
Sequence total quantity: 11
SEQ ID NO: 1            moltype = RNA  length = 20
FEATURE                 Location/Qualifiers
source                  1..20
                        mol_type = other RNA
                        organism = synthetic construct
SEQUENCE: 1
ggaatccctt ctgcagcacc                                            20

SEQ ID NO: 2            moltype = RNA  length = 20
FEATURE                 Location/Qualifiers
source                  1..20
                        mol_type = other RNA
                        organism = synthetic construct
SEQUENCE: 2
gggtgggggg agtttgctcc                                            20

SEQ ID NO: 3            moltype = RNA  length = 20
FEATURE                 Location/Qualifiers
source                  1..20
                        mol_type = other RNA
                        organism = synthetic construct
```

-continued

```
SEQUENCE: 3
ggtggacaag cggcagatag                                           20

SEQ ID NO: 4        moltype = DNA  length = 20
FEATURE             Location/Qualifiers
source              1..20
                    mol_type = other DNA
                    organism = synthetic construct
SEQUENCE: 4
acacgacgct cttccgatct                                           20

SEQ ID NO: 5        moltype = DNA  length = 13
FEATURE             Location/Qualifiers
source              1..13
                    mol_type = other DNA
                    organism = synthetic construct
SEQUENCE: 5
agatcggaag agg                                                  13

SEQ ID NO: 6        moltype = DNA  length = 32
FEATURE             Location/Qualifiers
source              1..32
                    mol_type = other DNA
                    organism = synthetic construct
SEQUENCE: 6
cttggcaccc gagaattcca nnnnnnnnnn nn                             32

SEQ ID NO: 7        moltype = DNA  length = 33
FEATURE             Location/Qualifiers
source              1..33
                    mol_type = other DNA
                    organism = synthetic construct
SEQUENCE: 7
cttggcaccc gagaattcca gggggggggg ggh                           33

SEQ ID NO: 8        moltype = DNA  length = 62
FEATURE             Location/Qualifiers
source              1..62
                    mol_type = other DNA
                    organism = synthetic construct
SEQUENCE: 8
aatgatacgg cgaccaccga gatctacaca cactctttcc ctacacgacg ctcttccgat  60
ct                                                              62

SEQ ID NO: 9        moltype = DNA  length = 57
FEATURE             Location/Qualifiers
source              1..57
                    mol_type = other DNA
                    organism = synthetic construct
SEQUENCE: 9
caagcagaag acggcatacg agatgtgact ggagttcctt ggcacccgag aattcca    57

SEQ ID NO: 10       moltype = DNA  length = 70
FEATURE             Location/Qualifiers
source              1..70
                    mol_type = other DNA
                    organism = synthetic construct
SEQUENCE: 10
aatgatacgg cgaccaccga gatctacacn nnnnnnaca ctctttccct acacgacgct  60
cttccgatct                                                      70

SEQ ID NO: 11       moltype = DNA  length = 65
FEATURE             Location/Qualifiers
source              1..65
                    mol_type = other DNA
                    organism = synthetic construct
SEQUENCE: 11
caagcagaag acggcatacg agatnnnnnn nngtgactgg agttccttgg cacccgagaa  60
ttcca                                                           65
```

CRISPR NUCLEASE OFF-TARGET DETECTION BY SEQUENCING (CROFT-SEQ)

SEQUENCE LISTING

The sequence listing entitled "CRISPR nuclease off-target detection by sequencing CROFT-Seq.xml", created on May 31, 2023, and having a file size of 10,730 bytes, is hereby incorporated by reference pursuant to 37 C.F.R. section 1.52(e) (5).

FIELD OF THE INVENTION

The field of disclosure related to in vitro methods for detecting double-strand breaks produced by genome editing nucleases, such as CRISPR-Cas9.

BACKGROUND OF THE INVENTION

The successful development of genome editing technology is critical not only for fundamental research to detect and quantify double strand breaks (DSBs) induced using programmable nucleases (CRISPR-Cas9 nucleases, Zinc-finger nucleases, TALE nucleases etc.), but especially for clinical applications to make the Cas9-based technology safer for genome editing and engineering. These nucleases are prone to cleave the DNA sites that are similar to the target sites, resulting in the chromosome rearrangements or mutations causing cell death or their transformation into cancer cells. State of the art methods for DSB detection lack appropriate level of sensitivity, are experimentally complex, lengthy, and costly. In order to make genome editing technology safer, it is crucial to utilize sensitive and more user-friendly in vitro method for DSB detection to evaluate the specificity and suitability of the selected nuclease.

Here we present rapid, cost-efficient, and user-friendly method (CRISPR nuclease off-target detection by sequencing or CROFT-seq) more suitable for simple, low budget laboratories and companies. In a prior publication (Young et al. (2019) Scientific reports), the CLEAVE-Seq method is described, whereas in CROFT-seq are included similar steps: dephosphorylation of dsDNA ends, DNA cleavage by Cas9 ribonucleoprotein (RNP) complex, biotinylated adapter ligation, affinity purification with streptavidin bead, synthesis of the non-biotinylated DNA strand, DNA library amplification. However, in CROFT-seq due to unique biotinylated adapter design and method steps conditions and composition DSB detection is easier, faster and cheaper compared to CLEAVE-seq and other in vitro methods. Detailed advantages of the invention will be apparent from the description, figures and claims.

SUMMARY OF INVENTION

The teachings provided herein are based on development and improvement of sensitive, rapid and cost-effective unbiased in vitro methods (with alternative step variations) for DSB detection produced using genome editing nucleases, such as CRISPR-Cas9.

Provided herein is the method for the detection of double strand breaks in dsDNA induced by programmable nucleases (e.g. CRISPR-Cas9); ligating an adapter to the cleaved DNA ends, where an adapter comprises a biotin for the purification of the ligated DNA, incubating the samples under conditions sufficient to remove of the unligated adapter with exonuclease I; and optionally fragmenting DNA with DNase I under conditions required to fragment DNA to an average length of about 100-500 bp; capturing ligated DNA on to streptavidin magnetic beads; adding the agent capable of removing non-biotinylated DNA strand (e.g. NaOH); optionally adding polyC tail to the 3'DNA end with terminal deoxynucleotidyl transferase (TdT) under conditions required to generate polyC tail of an average length of about 10-50 nt; synthesizing complementary strands using non-biotinylated strand synthesis primers compatible for use in PCR library amplification and sequencing; amplifying, pooling and purifying the library; and sequencing those libraries.

In some embodiments, the method can include dsDNAs: synthetic genomic DNA, gDNA from a cell type of interest, plasmid DNA.

In some embodiments, the DSB inducing agent is selected from the group consisting of: zinc-finger nucleases, mega-nucleases, transcription activator (TALEN), CRISPR-Cas RNA-guided nucleases.

In some embodiments, the DSB inducing agent is ribonucleoprotein (RNP) complex comprising a Cas9 endonuclease and a single-guide RNA (sgRNA).

In some embodiments, the DSB inducing agent is ribonucleoprotein (RNP) complex comprising an engineered Cas9 variant and a single-guide RNA (sgRNA).

In some embodiments, the adapter comprises a next generation sequencing primer sequence, a randomized DNA barcode.

In some embodiments, the non-biotinylated strand synthesis primers comprise a next generation sequencing primer sequence, a randomized DNA barcode or unique molecular identifier (UMI).

In some embodiments, the DNA is isolated from a mammalian, bacterial, plant, yeast or fungal cell (e.g., gDNA).

In some embodiments, the DNA is synthetic.

The method provided here improves the ability to detect double strand breaks induced by genome editing nucleases. Also, it has advantages over other in vitro and in vivo off-target detection methods. For example, the presented method is in vitro and contrary to in vivo methods off-target detection does not depend on chromatin state or transfection and expression of engineered nuclease and its components into cells. Furthermore, the presented method does not require serial library purification steps with magnetic beads The method described with scientific terms and references here will be understood by the person skilled in the invention relevant art. Various changes in form of details or methods and materials known in the art can be made therein without deflecting from the scope of the method. For instance, there may be examples described below using a specific Cas9 nuclease, other Cas9 nucleases from different organisms may be applied.

DESCRIPTION OF DRAWINGS

FIG. 3 shows a selection of results for FANCF off-target detection using CROFT-Seq version 1.

FIG. 4 shows a selection of results for FANCF off-target detection using CROFT-Seq version 2.

FIG. 5 shows a selection of results for VEGFA1 off-target detection using CROFT-Seq version 1.

FIG. 6 shows a selection of results for VEGFA1 off-target detection using CROFT-Seq version 2.

FIG. 7 shows a selection of results for XRCC5 off-target detection using CROFT-Seq version 1.

3

Figure 1:
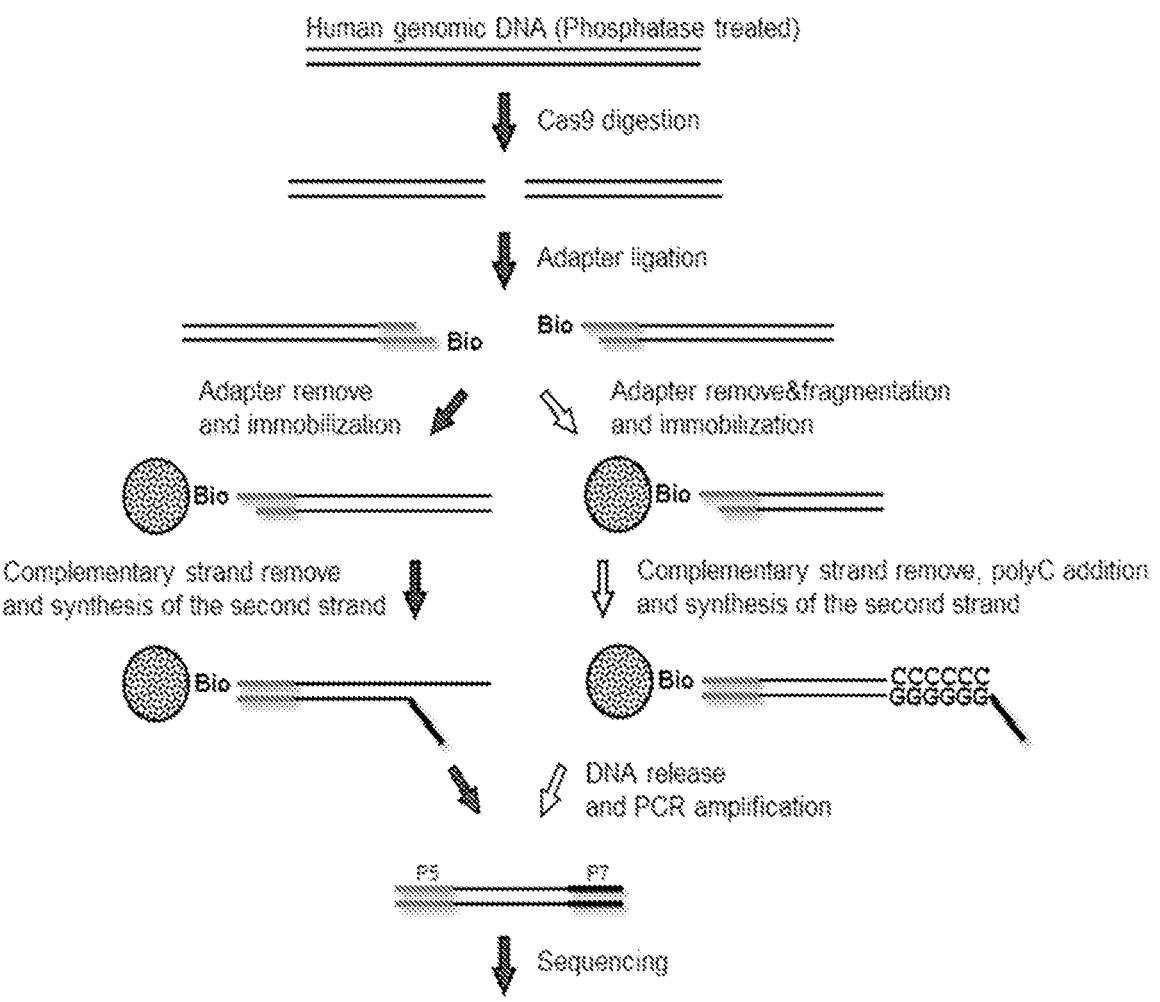
FIG. 1 shows a summary scheme of the method.

FIG. 8 shows a selection of results for XRCC5 off-target detection using CROFT-Seq version 2.

DETAILED DESCRIPTION OF THE INVENTION

Programmable genome editing nucleases such as CRISPR-Cas9 possess huge potential in personalized medicine and brought a broad interest in the scientific community. These enzymes allow rapidly and precisely correct gene mutations in genomic DNA. This is possible because the eukaryotic cell can precisely repair induced DNA breaks by homologous recombination. However, unintended cleavage may occur at different off-target sites, where even a low frequency cleavage can lead to unnecessary or even harmful gene mutations. To date, there are various cell culture-based and cell-free methods developed for detecting off-target cleavage sites produced by genome editing nucleases. Cell culture-based methods, for example, WGS (whole genome sequencing), which sequences the whole genome before and after gene editing, GUIDE-Seq (genome-wide unbiased identification of DSBs enabled by sequencing), which relies on integration of double strand oligonucleotides (dsODNs) into DSBs, BLESS (breaks labeling, enrichment on streptavidin and next generation sequencing), which captures DSBs in situ by biotinylated adaptors, IDVL (integrase defective lentiviral vector), which relies on integration of IDLV into DSBs, and DISCOVER-Seq (discovery of in situ Cas off-targets and verification by sequencing), which utilizes DNA repair protein MRE11 to identify DSBs in vivo (Guo et al. (2023) Front Bioeng Biotechnol). These methods can directly show off-target events in cells, however there are a number of limitations including high false negative rates, low integration of dsODN, low sensitivity, detects DSBs only at the sample preparation moment, depends on chromatin context and are expensive.

On the other hand, cell-free methods have advantages over cell-based methods, because these methods use purified genomic DNA and do not rely on cell-based limitations including cell transfection efficiency, chromatin structure, DNA repair mechanisms and it is easy to vary nuclease, genomic DNA concentration and cleavage time. To date, there are many described cell-free genome-wide off-target identification assays, for example, Digenome-Seq (digested genome sequencing), which relies of sequencing adapter ligation to all free DNA ends, SITE-Seq (selective enrichment and identification of tagged genomic DNA ends by sequencing), which captures repaired DNA ends with biotinylated adapter, CIRCLE-Seq (circularization for in vitro reporting of cleavage effects by sequencing), which relies of circularization of genomic DNA, RGEN-Seq (PCR-free next-generation sequencing method), which relies of sequencing adapter ligation to DNA without PCR amplification step and CLEAVE-Seq, which relies on dephosphorylation of free DNA ends prior DNA cleavage with nuclease and blunt end adapter ligation (Guo et al. (2023) Front Bioeng Biotechnol). These methods can detect much more potential off-target sites than cell-based methods, however, there are some limitations. For example, Digenome-Seq requires huge amount of reads per sample (>400 million reads), because high background of randomly sheared DNA is sequenced. SITE-Seq, CIRCLE-Seq, RGEN-Seq and CLEAVE-Seq lacks sensitivity and shows low validation rate. Nevertheless, these methods are labor intensive, time consuming and expensive. Also, these methods usually require DNA shearing and many DNA purification steps with magnetic beads.

4

Figure 2:
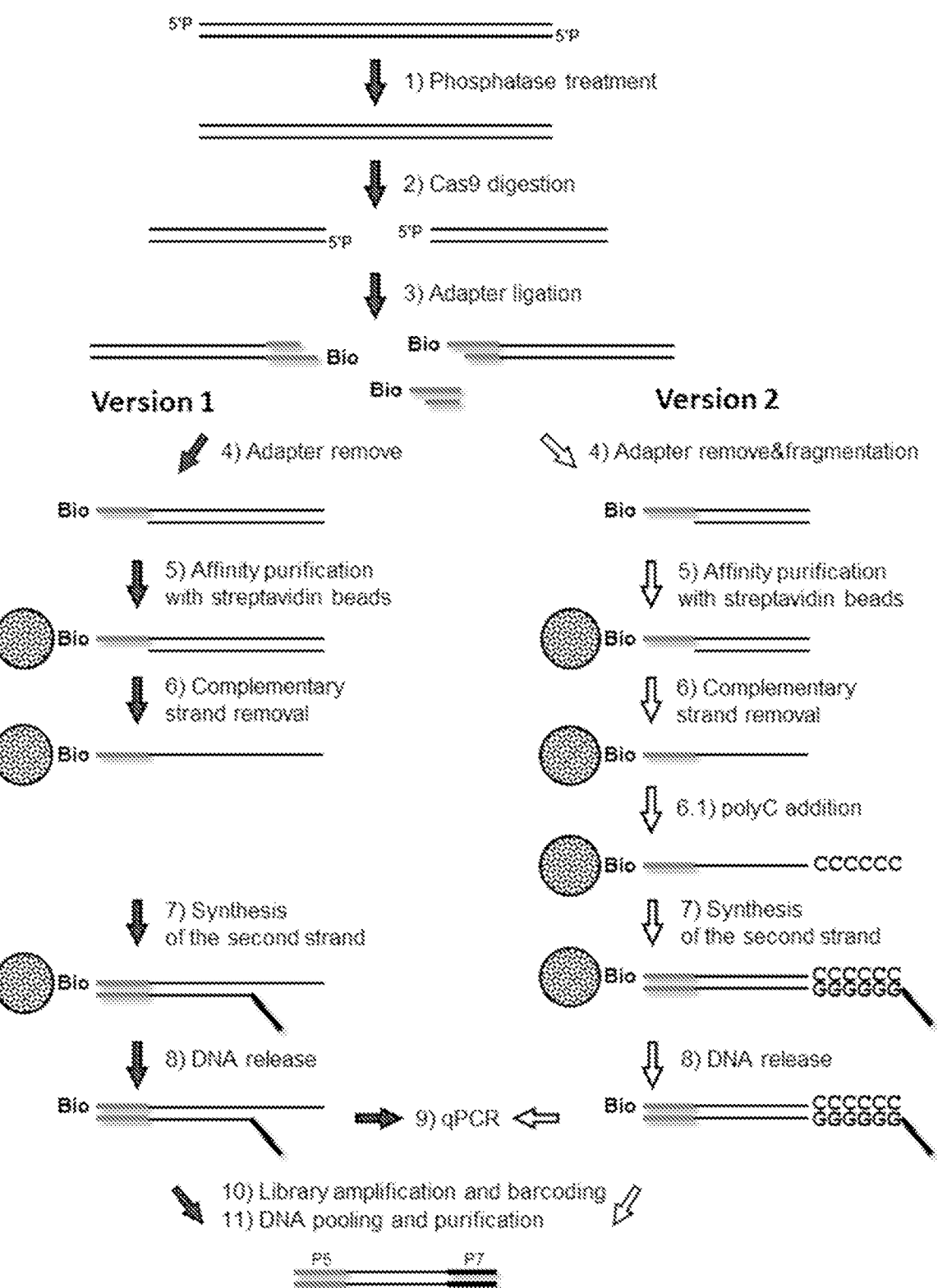
FIG. 2 shows a detailed schematic of the method.

Described herein is novel cell-free method CROFT-Seq (CRISPR nuclease off-target detection by sequencing) with two versions, which provides sensitive detection of off-target sites, induced by CRISPR/Cas9 nuclease in human genomic DNAs (FIG. 2). Similar to the CLEAVE-Seq method (Young et al. (2019) Sci Rep 9, 6729, US patent application US20210147909A1 filled on May 10, 2019), CROFT-Seq is based on dephosphorylation of randomly broken DNA ends prior digestion with nuclease enzyme, which subsequently prevents adapter ligation. This is achieved by treating genomic DNA with phosphatase, which significantly reduces free DNA ends containing phosphates. Then DNA is treated with genome editing nuclease, such as CRISPR/Cas9 nuclease, producing cleavage products mostly with blunt-end termini with 5' phosphate groups (Gasiunas et al. (2012) Proc Natl Acad Sci USA 109(39): E2579-86, Jinek et al. (2012) Science 337(6096):816-21). Cleavage products then can be selectively ligated to the non-phosphorylated adapter (one blunt-end and other sticky-end with 5'biotin). After that, unligated adapter is removed at optimal conditions, where DNA strands of the unligated adapter separates and are removed with single stranded DNA exonuclease. This eliminates any need of adapter removal using magnetic beads that is popular in other in vitro off-target detection methods. Also, it eliminates high background noise, which may arise from residual unligated adapter. Alternatively, in CROFT-Seq version 2, during adapter removal ligated DNA can be shredded to 100-500 bp under required conditions with deoxyribonuclease, which is necessary for further steps. In the next step, ligated DNA cleavage products with biotinylated adapter are purified using streptavidin coated magnetic beads. DNA immobilization onto magnetic beads allows easily change to any desirable buffer composition for further applications with very minimal DNA loss. Other in vitro methods use serial bead purification steps, such as CIRCLE-Seq or SITE-Seq to change buffer composition, where DNA is significantly lost and it is time consuming (Young et al. (2019) Sci Rep 9, 6729, Cameron et al. (2017) Nat Methods 14, 600-606). In the next step, non-biotinylated DNA strand is removed under conditions (i.e., with NaOH) necessary to separate DNA strands. This allows removing of DNA that is not necessary and may interfere in further steps. Alternatively, in CROFT-Seq version 2, after complementary strand removal polyC tail of 10-50 nt in length is added by terminal deoxynucleotidyl transferase to the 3' end of ssDNA. Then immobilized ssDNA from both versions of CROFT-Seq is used for non-biotinylated strand synthesis by T4 DNA polymerase. Additionally, in CROFT-Seq version 1, the non-biotinylated strand synthesis primer contains a 12 N nucleotide sequence (where N is A, G, C or T), which may be used as unique molecular identifier (UMI) enabling the accurate bioinformatic identification of PCR duplicates. Resulting DNA is then released from streptavidin coated magnetic beads and amplified by PCR for high throughput sequencing. A method for detecting double strand breaks in DNA, wherein cleavage of the DNA is induced by programmable nucleases, the method comprises:

ligating an adapter to the cleaved DNA ends, wherein an adapter comprises a biotin for the purification of the ligated DNA;

incubating the ligated DNA under conditions sufficient to remove the unligated adapter with exonuclease I;

capturing ligated DNA on the streptavidin-coated magnetic beads;

adding the agent capable of removing non-biotinylated DNA strand (e.g., NaOH) unattached to the streptavidin-coated magnetic beads;

synthesizing complementary strands using non-biotinylated strand synthesis primers compatible for use in PCR library amplification and sequencing;

amplifying, pooling and purifying the PCR libraries; and sequencing said PCR libraries.

Validation results of CROFT-Seq using SpCas9 showed that more than 20% of top5% off-target sites (include the off-targets whose read counts are above the 5% threshold of the read counts of top1 off-target site from the list) identified by CROFT-Seq were also edited in vivo (FIG. 3-8). However, validated off-target sites not always correlated with read count of off-target sites identified with in vitro CROFT-Seq. This phenomenon is also observed in other in vitro CIRLCE-Seq or SITE-Seq off-target methods, because different gene locations are impacted by various factors, such as chromatin accessibility, DNA repair or different concentrations of Cas9 and sgRNA in the cell. However, validation

6 vitro off-target detection methods such as CIRCLE-Seq or SITE-Seq, because it produces approximately 10 times more reads of detected off-target sites. Furthermore, CROFT-Seq can be performed using as low as 10 ng of human genomic DNA, making it an effective tool to detect off target sites in various cells and tissues, where DNA isolations produce very low yields. Low cost, time effectiveness, high sensitivity and comfortable automation possibility makes CROFT-Seq a powerful and attractive tool identifying off-target sites of genome editing nucleases.

The term "genome editing nucleases" as used herein refers to any composition which produces a double-strand break in a target sequence in the genome of an organism. Genome editing nucleases may be proteins that include but are not limited to: endonucleases such as zinc finger nucleases (Kim et al. (1996), Proc Natl Acad Sci USA 93(3): 1156-60), meganucleases (Silva et al. (2011) Curr Gene Ther 11(1):11-27, TALENs (Christian et al. (2010) Genetics 186 (2):757-61), CRISPR/Cas9 nucleases (Hsu et al. (2014) Cell 157, 1262-1278).

```
SEQ ID NO: 1 is the sequence of SpCas9 sgRNA RNA, targeting site in FANCF gene.
5'-GGAAUCCCUUCUGCAGCACC+ Synthego EZ Scaffold-3'

SEQ ID NO: 2 is the sequence of SpCas9 sgRNA RNA, targeting site in VEGFA1 gene.
5'-GGGUGGGGGGAGUUUGCUCC+ Synthego EZ Scaffold-3'

SEQ ID NO: 3 is the sequence of SpCas9 sgRNA RNA, targeting site in XRCC5 gene.
5'-GGUGGACAAGCGGCAGAUAG+ Synthego EZ Scaffold-3'

SEQ ID NO: 4 is the sequence of biotinylated upper strand DNA sequence of adapter.
5'-Biotin-ACACGACGCTCTTCCGATCT-3'

SEQ ID NO: 5 is the sequence of bottom strand DNA of adapter.
5'-AGATCGGAAGAGG-3'

SEQ ID NO: 6 is the sequence of NNN oligonucleotide for non-biotinylated strand
synthesis containing 12 N (N is either A, G, C or T) nucleotides at the 3'end.
5'-CTTGGCACCCGAGAATTCCANNNNNNNNNNNNN-3'

SEQ ID NO: 7 is the sequence of GGG oligonucleotide for non-biotinylated strand
synthesis containing 12 G nucleotides and 1 H (H is either A, C or T) nucleotide at
the 3'end.
5'-CTTGGCACCCGAGAATTCCAGGGGGGGGGGGGH-3'

SEQ ID NO: 8 is the sequence of forward DNA strand oligonucleotide for qPCR. N is
either A, C or T.
5'-AATGATACGGCGACCACCGAGATCTACACACACTCTTTCCCTACACGACGCTCTTCCGATCT -3'

SEQ ID NO: 9 is the sequence of reverse DNA strand oligonucleotide for qPCR.
5'-CAAGCAGAAGACGGCATACGAGATGTGACTGGAGTTCCTTGGCACCCGAGAATTCCA-3'

SEQ ID NO: 10 is the sequence of forward DNA strand indexing oligonucleotide containing
8 N (N is either A, G, C or T) nucleotides.
5'-AATGATACGGCGACCACCGAGATCTACACNNNNNNNNACACTCTTTCCCTACACGACGCTCTTCCGATCT-3'

SEQ ID NO: 11 is the sequence of reverse DNA strand indexing oligonucleotide containing
8 N (N is either A, G, C or T) nucleotides.
5'-CAAGCAGAAGACGGCATACGAGATNNNNNNNNGTGACTGGAGTTCCTTGGCACCCGAGAATTCCA-3'
``` rate of specific DSB nuclease or sgRNA could indicate their suitability for genome editing in future.

CROFT-Seq method uses individual enzymes, reagents and buffers with known composition, which are tested and optimized for each of CROFT-Seq step. This let significantly reduce price per sample and time to perform the whole method compared to commercial kits with proprietary and undisclosed composition. Also, the method does not require DNA library purifications steps with magnetic beads as CIRCLE-Seq (Young et al. (2019) Sci Rep 9, 6729) or SITE-Seq (Cameron et al. (2017) Nat Methods 14, 600-606), making it very suitable for automation. For therapeutic perspective, CROFT-Seq outperforms other sensitive in Embodiments of the Invention The invention is further described in the following examples, which are offered for illustrative purposes only, and are not intended to limit the scope of the invention in any way.

In the following examples *S. pyogenes* Cas9 was utilized as the DSB agent.

Cell Culture and Transfection

Wild-type HEK293T cells (ATCC) were cultured in DMEM medium with high glucose, sodium pyruvate and GlutaMAX (Thermo Fisher Scientific), supplemented with 10% FBS (Sigma) and penicillin/streptomycin at 37° C. and 5% $CO_2$. All cells were maintained at confluency below 80%. Cells were plated in a 12-well plate with approximately 250,000 cells per well in 500 μL culture medium one day before transfection. All transfections were performed with 3.6 μL TurboFect transfection reagent (Thermo Fisher Scientific) per 1.4 μg of plasmid encoding only Cas9 or Cas9 and sgRNA per 180 μL volume of DMEM medium. The transfected cells were collected 3 days post transfection. Genomic DNA was purified with GeneJET Genomic DNA Purification Kit ((Thermo Fisher Scientific) and quantified by Qubit 4.0 fluorimeter (Thermo Fisher Scientific).

CROFT-Seq Library Preparation (Brief)

CROFT-Seq (version 1&2) experiments with FANCF, VEGFA1 and XRCC5 sgRNAs or without sgRNAs were performed on purified genomic DNA from HEK293T cells or on commercial human genomic DNA (roche). Genomic DNA was treated with Thermosensitive Alkaline Phosphatase (Thermo Fisher Scientific). In vitro cleavage reactions were performed in a 40 μl reaction volume containing 100 nM SpCas9, 100 nM commercial sgRNA and 1 μg of human genomic DNA. Digested products were ligated to biotinylated adapter and treated with Exonuclease I (Thermo Fisher Scientific) and additionally with DNase I (Thermo Fisher Scientific) (only for CROFT-Seq version 2). Ligated DNA products were immobilized on streptavidin coated MyOne C1 magnetic beads (Thermo Fisher Scientific). Complementary DNA strand was removed with NaOH and additionally polyC tail was added to the 3' end of DNA with terminal deoxynucleotidyl transferase (Thermo Fisher Scientific) (only for CROFT-Seq version 2). The non-biotinylated DNA strand was synthesized using DNA oligonucleotide and T4 DNA polymerase (Thermo Fisher Scientific). Then, DNA was removed from magnetic beads and amplified by PCR using Phusion Plus DNA polymerase (Thermo Fisher Scientific). Completed libraries were quantified by bioanalyzer 2100 (Agilent) and sequenced with 100 bp paired end reads on an Illumina NextSeq 550 or 2000 platform. Detailed protocols for CROFT-Seq library construction are provided in Example 6.

RhAmpSeq Deep Sequencing

HEK293T cells were transfected with plasmids expressing Cas9 and sgRNAs as described above. Off-target lists for each sgRNA were identified by CROFT-Seq and the top 5% off-targets calculated from the top 1 off-target site read depth were selected for validation (FIG. 3-8). A total of 212 off-target sites (including on-target sites) were selected for three target sites (FANCF, VEGFA1 and XRCC5). PCR rhAmpSeq primers were successfully designed for all 212 sites and ordered from Integrated DNA technologies (IDT). According to the manufacturer's protocol, rhAmpSeq PCR libraries were amplified from 25 ng of purified HEK293T genomic DNA dublicates using rhAmpSeq CRISPR library kit (IDT). Resulting PCR products were pooled into different libraries corresponding to different sgRNA used transfection and purified with Ampure XP magnetic beads (Agencourt). Resulting rhAmpSeq libraries were quantified and analyzed with Agilent Bioanalyzer 2100 (Agilent) and sequenced on a NextSeq 2000 sequencer with more than 300000 average read depth. Sequenced data is analyzed with rhAmpSeq CRISPR analysis tool (www.eu.idtdna.com/pages/tools/rhampseq-crispr-analysis-tool).

CROFT-Seq Data Analysis

The analysis started with pair-end reads that were used as initial data. The removal of residual adapter sequences and low-quality reads was performed using Adapter Removal utilizing default parameters and appropriate adapter pairs specified in the method. The cleaned reads were aligned to the genome using BWA-MEM, followed by sorting and indexing with Samtools. The alignment file generation and manipulation were executed using default options. For each cleavage site search experiment, there were three targets and three control samples. Initially, each of the six samples were analyzed independently using the "find-cleavage-patterns.jl" script (www.github.com/agrybauskas/croft-seq-analysis). This script utilizes a reading frame of 4 bp in length to search for read start positions in the aligned R1 reads. If quantity of the read starts within the reading frame range is greater or equal to 20, the region is included for further analysis. From each included region, the cleavage position is selected based on the presence of forward and reverse read directions, or if absent, the position with highest amount of read starts. Subsequently, the target sequence is searched around the chosen cleavage position using the Needleman-Wunsch algorithm (realized in package "BioJulia/BioAlignments.jl") and the best potential alignment position for the sequence is recorded in BED format file. After all the six samples were analyzed individually, the results were combined using "combine-cleavage-patterns.jl" script. The target and control samples were combined separately. The aim of this combination process was to determine if the identified cleavage sites are consistently found within their respective sample groups. The cleavage site is considered to be found if the exact cleavage position is present in all three samples, both for the target and control samples. Following the combinations, the cleavage sites found in the control samples were excluded from the target samples. The deduction process was performed using the same script as in the combination step. The final list of potential on/off-target regions is output in BED format file.

Example 1. Method for the Identification and Characterization of a Double-Strand Break (CROFT-Seq)

In this example we describe a detailed in vitro CROFT-Seq (version 1&2) assay for finding cleavage sites of CRISPR/Cas9 nuclease in human genomic DNAs. If it is not indicated otherwise, each step in this example is performed for both CROFT-Seq versions 1&2. A DNA sample such as HEK293T isolated and purified (see cell culture and transfection) or commercial human genomic DNA (Roche) was cleaved with a Cas9 endonuclease with or without sgRNA RNP complex. In other embodiments, a different engineered Cas9 endonuclease may be used to cleave genomic DNA.

1. Treatment of Genomic DNA with FastAP 0.01-1 μg of human genomic DNA was treated with 2 units of Thermosensitive Alkaline Phosphatase (Thermo Fisher Scientific) in 20 μl 1×FastAP buffer (10 mM Tris-HCl (pH 8.0 at 37° C.). 5 mM $MgCl_2$, 100 mM KCl, 0.02% (v/v) Triton X-100 and 0.1 mg/ml BSA) at 37° C. for 10 minutes, followed by enzymatic inactivation at 80° C. for 10 minutes. The addition of phosphatase reduces the presence of phosphates at randomly broken DNA ends to which adapter can ligate.

2. Digestion of FastAP Treated gDNA with RNP Complex

Catalytically active Cas9-sgRNA complex was assembled in vitro by mixing Cas9 and different single-guide RNAs (sgRNAs) (SEQ ID NO:1-3) at 1:2 molar ratio in a 1×SB buffer (10 mM Tris-HCl (pH 7.5 at 37° C.), 100 mM NaCl and 1 mM DTT) and pre-incubated at 37° C. for 30 minutes. The final RNP concentration varied from 20-2000 nM. In one aspect, the relative concentrations of Cas9 and sgRNA were 200 nM Cas9 and 400 nM sgRNA.

The respective RNP complex (20 μl) was mixed with 20 μl reaction of dephosphorylated human gDNA. The reactions were incubated at 37° C. for 60 minutes, followed by enzymatic inactivation at 80° C. for 20 minutes.

3. Adapter Ligation

After DNA cleavage with Cas9, products are mostly produced with blunt-end termini (Gasiunas et al. (2012) Proc Natl Acad Sci USA 109(39):E2579-86, Jinek et al. (2012) Science 337(6096):816-21). In this example, a non-phosphorylated adapter (one blunt-end and other sticky-end with 5'biotin) is used to selectively ligate to the blunt-ended termini of cleavage products.

An adapter was assembled in the 0.2×buffer G (Thermo Fisher Scientific) mixing 20 μM biotinylated adapter upper strand (SEQ ID NO: 4 with 20 μM adapter bottom strand (SEQ ID NO: 5). Adapter oligos annealed by incubating reaction mixture at 95° C. for 5 minutes and allowed to slowly (−0.1° C./5 seconds) cool to 25° C.

Adapter ligation reaction was prepared as follows: 40 μl of cleaved gDNA was mixed with 40 μl 2×ligation reaction mix (50 mM Tris-HCl (pH 8.0 at 37° C.). 20 mM MgCl₂, 1 mM ATP, 2 mM DTT, 10% (w/v) PEG 4000, 200 nM adapter, and 20 U T4 DNA ligase (Thermo Fisher Scientific)). Ligation reaction was incubated at 22° C. for 15 minutes, followed by enzymatic inactivation at 80° C. for 10 minutes.

4. Adapter Removal

For CROFT-Seq version 1, adapter was removed by adding 1 μl of Exonuclease I (20 U) to the ligation reaction mix and incubated at 37° C. for 15 minutes. Reaction was stopped by adding 30 mM EDTA.

For CROFT-Seq version 2, unligated adapter was removed by adding 1 μl of Exonuclease I (20 U) to the ligation reaction mix and incubated at 37° C. for 20 minutes. Then added 0.001 U DNase I and incubated at 37° C. for an additional 10 minutes. Reaction was stopped by adding 30 mM EDTA.

5. Affinity Purification with Streptavidin Beads

In this step, ligated DNA cleavage products with biotinylated adapter were purified using streptavidin coated magnetic beads.

2×Bind and Wash (B&W) buffer with and without Tween 20 for binding and bead wash was prepared as follows: 10 mM Tris-HCl (pH 8.0 at 37° C.), 2 M NaCl, 1 mM EDTA and 0.1% (v/v) Tween 20 if required.

Streptavidin coated MyOne C1 magnetic beads (Thermo Fisher Scientific) were removed from storage at 4° C. and mixed by gentle inversion. One volume (5 μl per reaction) of MyOne C1 Dynabeads® was mixed with one volume (5 μl) of 2×B&W buffer with Tween 20. The washed bead mixture was placed on a magnetic stand and allowed to pellet for approximately 1 minute. The supernatant was removed. The washed beads were resuspended in 85 μl of 2×B&W buffer with Tween 20, to which 85 μl of adapter-ligated DNA (after adapter removal step) was added.

The bead/DNA mixture was incubated at room temperature (~22° C.) for 15 minutes. The samples were placed on a compatible magnetic stand. Beads were allowed to pellet for 1 minute, and the supernatant was removed. The beads were first washed by adding 50 μl of 1×B&W buffer with Tween 20, mixed and collected by centrifugation with mini-centrifuge/vortex (Biosan). Mixed samples were placed back on magnetic stand and allowed to pellet for 1 minute, and the supernatant was removed. The second bead wash was performed with 1×B&W buffer without Tween 20 in the same way as the first wash. The third bead wash was performed with miliQ H₂O in the same way as the first wash.

The washed beads with immobilized ligated DNA fragments were further processed in the complementary strand removal step.

6. Complementary Strand Removal 0.125 M NaOH solution was prepared as follows: required amount of NaOH (Roth) was dissolved in miliQ water.

For CROFT-Seq version 1, the washed beads with immobilized ligated DNA fragments were resuspended in 40 μl of 0.125 M NaOH solution, mixed and incubated at room temperature for 10 minutes. The samples were placed on a compatible magnetic stand. Beads were allowed to pellet for 1 minute, and the supernatant was removed. The beads were first washed by adding 40 μl of 0.125 M NaOH solution, mixed and collected by centrifugation with mini-centrifuge/vortex (Biosan).

Mixed samples were placed back on magnetic stand and allowed to pellet for 1 minute, and the supernatant was removed. The second bead wash was performed with 1×B&W buffer with Tween 20 in the same way as the first wash. The third bead wash was performed with 1×T4 DNA polymerase buffer in the same way as the first wash. The washed beads were removed from magnetic stand and resuspended in 30 μl 1×T4 DNA polymerase buffer, mixed and collected by centrifugation with mini-centrifuge/vortex (Biosan).

For CROFT-Seq version 2, complementary strand removal, first and second bead washes were performed as described for CROFT-Seq version 1. The third bead wash was performed by adding 1×FastAP buffer, mixed and collected by centrifugation with mini-centrifuge/vortex (Biosan). Mixed samples were placed back on magnetic stand and allowed to pellet for 1 minute, and the supernatant was removed. The washed beads were removed from magnetic stand and resuspended in 30 μl 1×FastAP buffer. Here, an additional 6.1 step (polyC tail addition) was performed. 30 μl of washed bead solution was mixed with 1 μl 10×FastAP buffer, 2 μl 10 mM dCTP and 6.5 μl miliQ H2O. Reactions were started with 0.5 μl TdT (10 U) (Thermo Fisher Scientific) and incubated at 37° C. for 15 minutes. The samples were placed on a compatible magnetic stand. Beads were allowed to pellet for 1 minute, and the supernatant was removed. The beads were first washed by adding 50 μl of 1×B&W buffer with Tween 20, mixed and collected by centrifugation with mini-centrifuge/vortex (Biosan). Mixed samples were placed back on magnetic stand and allowed to pellet for 1 minute, and the supernatant was removed. The second bead was performed with 1×B&W buffer without Tween 20 in the same way as the first wash. The third bead wash was performed with 1×T4 DNA polymerase buffer in the same way as the first wash. The washed beads were removed from magnetic stand and resuspended in 30 μl 1×T4 DNA polymerase buffer, mixed and collected by centrifugation with mini-centrifuge/vortex (Biosan).

7. Synthesis of the Non-Biotinylated Strand

50% (w/v) PEG 8000 solution was prepared as follows: required amount of PEG 8000 (Roth) was dissolved in miliQ H2O.

The resuspended beads (30 μl) from the step 6 were mixed with 4 μl 5×T4 DNA polymerase buffer, 8 μl 50% (w/v) PEG 8000, 1.25 μl 10 μM NNN oligonucleotide (SEQ ID NO:6) for CROFT-Seq version 1 or 1.25 μl 10 μM GGG oligonucleotide (SEQ ID NO:7) for CROFT-Seq version 2 and 2.3 μl miliQ H2O.

The reaction mix was mixed by vortexing and beads collected by centrifugation with mini-centrifuge/vortex (Biosan). Reactions were incubated at 98° C. for 1 minute in a thermocycler (Eppendorf) and let slowly (−0.5° C./second) cool down to 25° C. Reactions were further incubated at 25° C. for 30 minutes. Then, 3.5 µl of 10 mM dNTP mix (Thermo Fisher Scientific) was added to each sample and mixed by pipetting. Reactions were started by adding 1 µl of T4 DNA polymerase (5 U) (Thermo Fisher Scientific) to each reaction, mixed by pipetting and incubated at 25° C. for 15 minutes.

8. DNA Release

The samples from the previous step were placed on a compatible magnetic stand. Beads were allowed to pellet for 1 minute, and the supernatant was removed. The beads were first washed by adding 50 µl of 1×B&W buffer with Tween 20, mixed and collected by centrifugation with mini-centrifuge/vortex (Biosan). Mixed samples were placed on magnetic stand and allowed to pellet for 1 minute, and the supernatant was removed. The second bead wash was performed in the same way with 1×B&W buffer without Tween 20. The third bead wash was performed in the same way with miliQ $H_2O$. The washed beads were removed from magnetic stand and resuspended in 40 µl miliQ H2O. Reactions were incubated at 70° C. for 5 minute in a thermocycler (Eppendorf) to release DNA from the beads. Then reactions were placed on magnetic stand and allowed to pellet for 1 minute. The supernatant with DNA was transferred to the new tube and the beads were discarded.

Example 2. qPCR

In this example, DNA fragments from DNA release step were amplified to determine the cycle number for library amplification and barcoding. The cycle number is determined as follows: First, the maximum fluorescence value was determined at which the fluorescence reached a plateu. Then, calculated at which cycle number 50% of maximum fluorescence is reached. Use the corresponding cycle number for the library amplification and indexing PCR.

A 15 µl quantitative polymerase chain reaction (qPCR) was assembled as follows: 8.5 µl supernatant (from DNA release step), 3 µl 5×Phusion Plus buffer (Thermo Fisher Scientific), 0.75 µl 10 µM qPCR forward primer (SEQ ID NO:8), 0.75 µl 10 µM qPCR reverse primer (SEQ ID NO:9), 0.3 µl 10 mM dNTP mix (Thermo Fisher Scientific), 0.15 µl 100×SYBR Green I solution (Thermo Fisher Scientific), 0.15 µl Phusion Plus DNA polymerase (0.3 U) (Thermo Fisher Scientific) and 1.4 µl miliQ $H_2O$. The qPCR reaction mixture was placed in the MIC qPCR cycler (Biomolecular Systems) with the following program:

1. 98° C. for 30 seconds
2. 98° C. for 10 seconds
3. 60° C. for 10 seconds
4. 72° C. for 30 seconds
Steps 2-4 were repeated 40 times in total
5. 72° C. for 2 minutes Example 3. Library Amplification and Barcoding 3 µM index primer mix was prepared as follows: 1.5 µl 100 µM forward indexing primer (SEQ ID NO:10), 1.5 µl 100 µM reverse indexing primer (SEQ ID NO:11), 47 µl miliQ $H_2O$. Primer mixes with different index sequences were aliquoted to 96 well plates and used for library barcoding.

A 30 µl indexing PCR reaction was assembled as follows: 17 µl supernatant (from DNA release step), 6 µl 5×Phusion Plus buffer (Thermo Fisher Scientific), 5 µl 3 µM indexing primer mix (SEQ ID NO:10-11), 0.6 µl 10 mM dNTP mix (Thermo Fisher Scientific), 0.3 µl Phusion Plus DNA polymerase (0.6 U) (Thermo Fisher Scientific) and 1.1 µl miliQ $H_2O$. The indexing PCR reaction mixture was placed in the thermal cycler (Eppendorf) with the following program:

1. 98° C. for 30 seconds
2. 98° C. for 10 seconds
3. 60° C. for 10 seconds
4. 72° C. for 30 seconds
Steps 2-4 were repeated N times (the cycle number is determined in example 5)
5. 72° C. for 2 minutes
6. Hold at 4° C.

Samples from indexing PCR step were pooled in separate pools for a total of 180-420 µl.

Example 4. Library Pool Cleanup

In this example, the pooled samples were cleaned at room temperature using purification module with magnetic beads (Lexogen).

Purification module with magnetic beads were removed from storage at 4° C. and equilibrated at room temperature for 30 minutes before use. Purification beads (PB) from the module were resuspended before adding them to the reaction. 1×volume of purification beads (PB) was added to the 1×volume of pooled samples, mixed and collected by centrifugation with mini-centrifuge/vortex (Biosan). The reaction mixture was incubated for 5 minutes. Then reactions placed in the magnetic stand and the beads collected for 1-2 minutes or until the supernatant is clear. The supernatant was removed. The beads were resuspended in 1×volume of elution buffer (EB), removed from magnetic stand and incubated for 2 minutes. 1×volume of purification solution (PS) was added to resuspended beads to re-precipitate the library. Mixed thoroughly and collected by centrifugation with mini-centrifuge/vortex (Biosan). Reactions incubated for 5 minutes. Then reactions placed back in the magnetic stand and the beads collected for 1-2 minutes or until the supernatant is clear. The supernatant was removed and the beads washed two times for 30 seconds with freshly prepared 500 µl 80% ethanol. The tubes were leaved in the magnetic stand and trace ethanol was allowed to evaporate for 5-10 minutes. The reactions were removed from magnetic stand and beads resuspended in 50 or 100 µl volume of miliQ $H_2O$ and incubated for 2 minutes. The reactions were placed back to the magnetic stand and the beads were allowed to collect for 1-2 minutes or until the supernatant is clear. The supernatant was transferred to a new tube and optionally stored at −20° C. prior library quantification and sequencing.

Example 5. Library Quantification and Quality Control

The library quantification was performed with Qubit 4.0 fluorometer (Invitrogen) and Qubit dsDNA HS Assay Kit (Thermo Fisher Scientific). For library quality control, 1 µl of library (from example 4) was loaded on an Agilent Bioanalyzer High Sensitivity DNA chip and analyzed with Agilent Bioanalyzer 2100.

Example 6. Protocols of CROFT-Seq Method

In this example, two versions of CROFT-Seq protocols (v1 and v2) for an in vitro assay for identification and characterization of double-strand breaks produced by CRISPR/Cas9 nucleases are described.

CROFT-Seq Protocol v1 (Additional Steps for Protocol v2 are Indicated)

Annealing of Adapter

The adapter (20 μM) was prepared by annealing of its upper (SEQ ID NO: 4) and bottom strands (SEQ ID NO: 5) (ratio 1:1) in the 0.2×buffer G.

Annealing program: 95° C. for 5 min, slowly (−0.1° C./5 seconds) cool to 25° C., hold at 4° C.

Assembly of RNP Complex

The 2×RNP complex was assembled in vitro by mixing Cas9 and sgRNA (1:2 molar ratio of Cas9:sgRNA) in a 1×SB buffer.

Incubation program: 37° C. for 30 min, hold at 4° C.

1. Treatment of Genomic DNA with FastAP

Human genomic DNA was dephosphorylated as follows. If more experiments were planned, a master mix was prepared, from which 15 μl was dispensed into individual PCR tubes.

| Component | Volume |
|---|---|
| MiliQ H$_2$O | 11 μl |
| FastAP buffer (10×) | 2 μl |
| FastAP (1 U/μl) | 2 μl |
| Total master mix | 15 μl |
| gDNA (0.01-1 μg) | 5 μl |
| Total | 20 μl |

Incubation program: 37° C. for 10 min, then 80° C. for 10 min, hold at 4° C.

2. Digestion of FastAP Treated gDNA with RNP Complex

20 μl of RNP complex (2×) was mixed with 20 μl of FastAP treated gDNA.

| Component | Volume |
|---|---|
| Prepared RNP complex (2×) | 20 μl |
| Dephosphorylated gDNA mix | 20 μl |
| Total | 40 μl |

Incubation program: 37° C. for 60 min, then 80° C. for 20 min, hold at 4° C.

3. Adapter Ligation

Cleaved gDNA fragments were ligated to biotinylated adapter as follows. If more experiments were planned, a master mix was prepared, from which 36 μl was dispensed into individual PCR tubes.

| Component | Volume |
|---|---|
| MiliQ H$_2$O | 18.72 μl |
| Tris-HCl (200 mM, pH 8.0) | 8 μl |
| Biotinylated Adapter (20 μM) | 0.4 μl |
| DTT (1M) | 0.08 μl |
| MgCl$_2$ (1M) | 0.4 μl |
| ATP (100 mM) | 0.4 μl |
| PEG 4000 (50% w/v) | 8 μl |
| Total master mix | 36 μl |
| Digested gDNA (from 2 step) | 40 μl |
| T4 DNA Ligase (5 U/μl) | 4 μl |
| Total | 80 μl |

Incubation program: 22° C. for 15 min, then 80° C. for 10 min, hold at 4° C.

4. Adapter Remove

Unligated adapter was removed as follows.

| Component | Volume |
|---|---|
| Ligated DNA (from 3 step) | 80 μl |
| Exonuclease I (20 U/μl) | 1 μl |
| Total | 81 μl |

Incubation program: 37° C. for 15 min, then add 5.2 μl of 0.5 M EDTA (to the total ~30 mM of EDTA).

For protocol v2:

| Component | Volume |
|---|---|
| Ligated DNA (from 3 step) | 80 μl |
| Exonuclease I (20 U/μl) | 1 μl |
| Total | 81 μl |

Incubation program: 37° C. for 20 min. Then proceed as indicated below.

| | |
|---|---|
| DNase I (0.001 U/μl) | 1 μl |
| Total | 82 μl |

Incubation program: 37° C. for 10 min, then add 5.2 μl of 0.5 M EDTA (to the total ~30 mM of EDTA).

5. Affinity Purification with Streptavidin Beads

DNA fragments were immobilized and purified with streptavidin coated magnetic beads (Dynabeads MyOne Streptavidin C1).

1. Prepare 2×Bind and Wash (B&W) buffer with and without Tween 20 for the affinity purification procedure with Dynabeads: 10 mM Tris-HCl (pH8.0 at 25° C.), 2 M NaCl, 1 mM EDTA with and without 0.1% Tween 20.

2. Remove the Dynabeads from 4° C., mix by gently inverting the tube.

3. Mix one volume (5 μl per reaction) of the Dynabeads with one volume (5 μl) of 2×B&W buffer with Tween 20. Mix by vortexing and spin down.

4. Place Dynabead mixture on magnetic stand and allow pelleting for 1 minute. Remove the supernatant.

5. Resuspend Dynabeads in 85 μl of 2×B&W buffer with Tween 20. Mix by vortexing and spin down.

6. Mix 85 μl of the prepared Dynabeads with 85 μl exonuclease I treated DNA (from step 4). Mix by vortexing and spin down. Incubate at room temperature (~22° C.) for 15 minutes.

7. After incubation, place samples on a compatible magnetic stand. Allow beads to pellet for 1 minute. Remove the supernatant.

8. Wash the beads with 50 μl of 1×B&W buffer with Tween 20. Mix by vortexing and spin down. Place samples back to the magnetic stand and allow pelleting for 1 minute. Remove supernatant.

9. Repeat step 8 using 1×B&W without Tween 20, then using miliQ H2O.

10. Proceed to the complementary strand removal (step 6).

6. Complementary Strand Removal

Non-biotinylated DNA strand (complementary strand) was removed using NaOH.

1. Resuspend washed beads (from step 5) in 40 μl of 0.125 M NaOH solution. Remove samples from the magnetic stand, mix by vortexing and spin down. Incubate at room temperature (~22° C.) for 10 minutes.

2. Place bead mixture back to the magnetic stand and allow pelleting for 1 minute. Wash the beads with 40 μl of 0.125 M NaOH solution. Place samples to the magnetic stand and allow pelleting for 1 minute. Remove supernatant.

3. Repeat step 2 using 1×B&W with Tween 20, then using 1×T4 DNA polymerase buffer.

4. Resuspend the beads in 30 μl 1×T4 DNA polymerase buffer. Remove samples from the magnetic stand, mix by vortexing and spin down.

For protocol v2: for wash and resuspension (3 and 4 steps) use 1×FastAP buffer instead of using 1×T4 DNA polymerase buffer). Proceed to 6.1 step.

Additional Step for Protocol v2:

6.1 PolyC Addition polyC tail was added to the 3' end of DNA as follows. If more experiments were planned, a master mix was prepared, from which 9.5 μl was dispensed into individual PCR tubes.

| Component | Volume |
|---|---|
| MiliQ H$_2$O | 6.5 μl |
| FastAP buffer (10×) | 1 μl |
| dCTP (10 mM) | 2 μl |
| Total master mix | 9.5 μl |
| NaOH treated DNA (from 6 step) | 30 μl |
| TdT (20 U/μl) | 0.5 μl |
| Total | 40 μl |

Incubation program: 37° C. for 15 min. Then proceed to bead wash and resuspension as indicated below.

1. Place bead mixture on magnetic stand and allow pelleting for 1 minute. Wash the beads with 40 μl of 1×B&W buffer with Tween 20. Mix by vortexing and spin down. Place samples to the magnetic stand and allow pelleting for 1 minute. Remove supernatant.

2. Repeat step 1 using 1×B&W without Tween 20, then using 1×T4 DNA polymerase buffer.

3. Resuspend the beads in 30 μl 1×T4 DNA polymerase buffer. Remove samples from the magnetic stand, mix by vortexing and spin down.

7. Non-biotinylated Strand Synthesis

The non-biotinylated DNA strand was synthesized as follows. If more experiments were planned, a master mix was prepared, from which 15.55 μl was dispensed into individual PCR tubes.

| Component | Volume |
|---|---|
| MiliQ H$_2$O | 2.3 μl |
| T4 DNA polymerase buffer (5×) | 4 μl |
| NNN oligo (or GGG oligo for protocol v2) (10 μM) | 1.25 μl |
| PEG 4000 (50% w/v) | 8 μl |
| Total master mix | 15.55 μl |
| DNA (from 6 step) (or from 6.1 step for protocol v2) | 30 μl |
| Total | 45.55 μl |

Incubation program: 98° C. for 1 minute, then let slowly (−0.5° C./second) cool down to 25° C. Reactions were further incubated at 25° C. for 30 minutes. Then proceed as indicated below.

| | |
|---|---|
| dNTP mix (10 mM) | 3.45 μl |
| T4 DNA polymerase (5 U/μl) | 1 μl |
| Total | 50 μl |

Incubation program: 25° C. for 15 minutes. Proceed to 8 step.

8. DNA Release

DNA was released from magnetic beads as follows.

1. Place bead mixture on magnetic stand and allow pelleting for 1 minute. Wash the beads with 50 μl of 1×B&W buffer with Tween 20. Mix by vortexing and spin down. Place samples in the magnetic stand and allow pelleting for 1 minute. Remove supernatant.

2. Repeat step 1 using 1×B&W without Tween 20, then using miliQ H$_2$O.

3. Resuspend the beads in 40 μl miliQ H$_2$O. Remove samples from the magnetic stand, mix by vortexing and spin down. Incubate at 70° C. for 5 minutes.

4. After incubation, place samples back to the magnetic stand. Allow beads to pellet for 1 minute. Collect the supernatant in the new tube.

9. qPCR

The cycle number required for library amplification and barcoding was determined as follows. If more experiments were planned, a master mix was prepared, from which 6.5 μl was dispensed into individual qPCR tubes.

| Component | Volume |
|---|---|
| MiliQ H$_2$O | 1.4 μl |
| Phusion Plus buffer (5×) | 3 μl |
| qPCR forward primer (10 μM) | 0.75 μl |
| qPCR reverse primer (10 μM) | 0.75 μl |
| dNTP mix (10 mM) | 0.3 μl |
| SYBR Green I solution (100×) | 0.15 μl |
| Phusion Plus DNA polymerase (2 U/μl) | 0.15 μl |
| Total master mix | 6.5 μl |
| Released DNA from beads (from 8 step) | 8.5 μl |
| Total | 15 μl | qPCR program: 98° C. for 30 s, 40 cycles of (98° C. for 10 s, 60° C. for 10 s, 72° C. for 30 s), 72° C. for 2 min.

10. Library Amplification and Barcoding

The reactions were amplified and barcoded as follows. If more experiments were planned, a master mix was prepared, from which 8 μl was dispensed into individual PCR tubes.

| Component | Volume |
|---|---|
| MiliQ H$_2$O | 1.1 μl |
| Phusion Plus buffer (5×) | 6 μl |
| dNTP mix (10 mM) | 0.6 μl |
| Phusion Plus DNA polymerase (2 U/μl) | 0.3 μl |
| Total master mix | 8 μl |
| index primer mix (3 μM) | 5 μl |
| Released DNA from beads (from 8 step) | 17 μl |
| Total | 30 μl |

PCR program: 98° C. for 30 s, N cycles (determined in the 9 step) of (98° C. for 10 s, 60° C. for 10 s, 72° C. for 30 s), 72° C. for 2 min, hold at 4° C. After PCR, samples were pooled in separate pools for a total of 180-420 μl.

11. Library Pool Cleanup

DNA pools were purified at room temperature (~22° C.) using purification module with magnetic beads (Lexogen).

1. Remove purification module with magnetic beads from 4° C. and equilibrate at room temperature for 30 minutes.
2. Resuspend purification beads (PB) from the module by gently inverting the tube.
3. Mix 1×volume of purification beads (PB) with 1×volume of the pooled samples. Mix by vortexing and spin down. Incubate for 5 minutes.
4. After incubation, place samples on a compatible magnetic stand. Allow beads to pellet for 1-2 minutes. Remove the supernatant.
5. Resuspend beads in 1×volume of elution buffer (EB). Remove samples from the magnetic stand, mix by vortexing and spin down. Incubate for 2 minutes.
6. Add 1×volume of purification solution (PS), mix by vortexing and spin down. Incubate for 5 minutes
7. Place samples back in the magnetic stand. Collect the beads for 1-2 minutes. Remove the supernatant.
8. Wash the beads two times for 30 seconds with freshly prepared 500 μl 80% ethanol. Remove supernatant.
9. Leave the tubes in the magnetic stand and let traces of ethanol evaporate for 5-10 minutes.
10. Remove the tubes from magnetic stand and resuspend beads in 50 or 100 μl volume of miliQ H$_2$O. Incubate for 2 minutes.
11. Place resuspended beads back in the magnetic stand and allow beads to collect for 1-2 minutes. Collect the supernatant to the new tube.

12. Library Quantification and Quality Control

Quantify the library using Qubit dsDNA HS Assay Kit (Thermo Fisher Scientific), according to the manufacturer instructions. Additionally perform library quality control as follows. Load 1 μl of the library (from 11 step) on an Agilent Bioanalyzer High Sensitivity DNA chip and analyzed with Agilent Bioanalyzer 2100, according to the manufacturer instructions.

Example 7. In Vivo Validation of Off-Target Sites Identified by CROFT-Seq in Human Cells To choose the most precise Cas9-guide RNA RNP complex for human genome editing it is important know if off-target sites identified by in vitro off-target identification method are actually edited in cells by these Cas9/gRNA complexes. Therefore, in this example we describe in vivo validation of off-target sites identified by novel in vitro CROFT-Seq method. Previously was shown what most off-target sites identified by both in vitro CIRCLE-Seq and in vivo GUIDE-Seq methods have high read counts (Young et al. (2019) Sci Rep 9, 6729, US patent application US20210147909A1 filled on May 10, 2019). This suggests what in vivo edited off-target sites are also often efficiently cleaved in vitro. In that respect, we have chosen to validate these identified off-target sites, which fall in top5% list according to read count (include the off-targets whose read counts are above the 5% threshold of the read counts of top1 off-target site from the list) (FIG. 3-8). The most of these off-target sites includes in both CROFT-Seq v1 and v2 methods.

To determine whether the selected off-target sites identified by CROFT-Seq v1 and v2 could be cleaved in human cells, we performed deep, targeted sequencing using rhAmpSeq technology (www.idtdna.com/pages/products/crispr-genome-editing/rhampseq-crispr-analysis-system). Using rhAmpSeq method, we validated a total of 207 off-target sites for FANCF, VEGFA1 and XRCC5 sgRNAs found by both CROFT-Seq v1 and v2 (FIG. 3-8). The percentage of edited cells there estimated by difference of average indel frequency between two positive reactions (cells treated with SpCas9 and sgRNA) and two negative reactions (cells treated only with SpCas9). Targeted deep sequencing revealed what 47 of 207 (22.7%) off-target sites identified are edited in the cell with indel frequencies more than 0.1%. Indel frequencies less than 0.1% is difficult to validate, because of the error rate of deep next-generation sequencing is approximately 0.1%. The indel frequencies identified here not always correlate with read count as it is also observed in other in vitro CIRLCE-Seq or SITE-Seq off-target methods, because genome editing in cells is impacted by chromatin accessibility, DNA repair and other cell related factors.

---

The invention claimed is:

1. A method for detecting double strand breaks in DNA, wherein cleavage of the DNA is induced by programmable nucleases, the method comprises:

a) ligating an adapter to the cleaved DNA ends, wherein an adapter comprises a biotin for the purification of the ligated DNA;

b) incubating the ligated DNA under conditions sufficient to remove the unligated adapter with exonuclease I;

c) capturing ligated DNA on the streptavidin-coated magnetic beads;

d) adding an agent capable of removing non-biotinylated DNA strand unattached to the streptavidin-coated magnetic beads;

e) synthesizing complementary strands using non-biotinylated strand synthesis primers compatible for use in PCR library amplification and sequencing;

f) amplifying, pooling and purifying the PCR libraries; and g) sequencing said PCR libraries.

2. The method of claim 1, wherein the DNA is one of dsDNA: synthetic genomic DNA, gDNA from a cell type of interest, or plasmid DNA.

3. The method of claim 2, wherein the DNA is isolated from a bacterial, mammalian, plant, yeast or fungal cell.

4. The method of claim 1, wherein the double strand break inducing agent is selected from the group consisting of: zinc-finger nucleases, meganucleases, transcription activator (TALEN), and CRISPR-Cas RNA-guided nucleases.

5. The method of claim 1, wherein the double strand break inducing agent is ribonucleoprotein (RNP) complex comprising a Cas9 endonuclease and a single-guide RNA (sgRNA).

6. The method of claim 1, wherein the double strand break inducing agent is ribonucleoprotein (RNP) complex comprising an engineered Cas9 variant and a single-guide RNA (sgRNA).

7. The method of claim 1, wherein the adapter comprises a next generation sequencing primer sequence or a randomized DNA barcode.

8. The method of claim 1, wherein the non-biotinylated strand synthesis primers comprise a next generation sequencing primer sequence, a randomized DNA barcode or unique molecular identifier (UMI).

9. The method of claim 1 for detecting double strand breaks in DNA, wherein cleavage of the DNA is induced by programmable nucleases, wherein the method further comprises:

between steps b) and c) fragmenting the ligated DNA with DNase I under conditions required to fragment DNA to an average length of about 100-500 bp;

in step c) capturing the ligated and fragmented DNA on the streptavidin-coated magnetic beads; and between steps d) and e) adding polyC tail to the 3'DNA end with terminal deoxynucleotidyl transferase (TdT) under conditions required to generate polyC tail of an average length of about 10-50 nt.

10. The method of claim 9, wherein the DNA is one of dsDNA: synthetic genomic DNA, gDNA from a cell type of interest, or plasmid DNA.

11. The method of claim 10, wherein the DNA is isolated from a bacterial, mammalian, plant, yeast or fungal cell.

12. The method of claim 11, wherein the double strand break inducing agent is selected from the group consisting of: zinc-finger nucleases, meganucleases, transcription activator (TALEN), and CRISPR-Cas RNA-guided nucleases.

13. The method of claim 11, wherein the double strand break inducing agent is ribonucleoprotein (RNP) complex comprising a Cas9 endonuclease and a single-guide RNA (sgRNA).

14. The method of claim 11, wherein the double strand break inducing agent is ribonucleoprotein (RNP) complex comprising an engineered Cas9 variant and a single-guide RNA (sgRNA).

15. The method of claim 11, wherein the adapter comprises a next generation sequencing primer sequence or a randomized DNA barcode.

16. The method of claim 11, wherein the non-biotinylated strand synthesis primers comprise a next generation sequencing primer sequence, a randomized DNA barcode or unique molecular identifier (UMI).

17. The method of claim 1, wherein the agent capable of removing non-biotinylated DNA strand is NaOH.

* * * * *